United States Patent [19]

Dixon

[11] Patent Number: 5,554,361

[45] Date of Patent: Sep. 10, 1996

[54] PROCESSED PRODUCT FOR SKIN AND HAIR TREATMENT

[76] Inventor: Gary W. Dixon, P.O. Box 5835, Kingsport, Tenn. 37663-0835

[21] Appl. No.: 377,501

[22] Filed: Jan. 24, 1995

Related U.S. Application Data

[63] Continuation-in-part of Ser. No. 184,839, Jan. 21, 1994, abandoned.

[51] Int. Cl.$^6$ .............................. A61K 7/42; A61K 7/48; A61K 33/18; A61K 35/60
[52] U.S. Cl. .................. 424/70.15; 424/59; 424/672; 424/523; 514/410
[58] Field of Search .................. 514/410; 424/59, 424/70, 70.15, 672, 523

[56] References Cited

U.S. PATENT DOCUMENTS

| | | | |
|---|---|---|---|
| 4,478,853 | 10/1984 | Chaussee | 424/358 |
| 5,023,235 | 6/1991 | N'Guyen et al. | 514/18 |
| 5,075,113 | 12/1991 | DuBois | 424/450 |

*Primary Examiner*—S. Mark Clardy
*Attorney, Agent, or Firm*—M. Alex Brown

[57] ABSTRACT

A processed product for hair and skin treatment, having binary and tertiary fluid phase levels prior to remixing and therapeutic use is disclosed. The invention discloses defined amounts of admixed components including an Iodine complex having tincture of iodine solution and povidone-iodine compound, a diluting fluid complex having a water and mineral oil constituent, and a cod liver oil component, which, after admixing, are ambiently exposed to a photon-light-energy component from sunlight or substantially equivalent artificial light to produce a processed product having at least binary product reaction fluid levels and containing a nucleophically iodinated cod liver oil compound. The composition is mixed prior to therapeutic application of targeted hair, skin, mucosal or internal areas of a human or animal, mixing the fluid levels to provide synergistic properties and enhanced delivery of the remaining iodine-reaction components and the iodinated cod liver oil compound contained in the product, enhancing the effect and delivery to targeted areas of vitamins A and D and other constituents in the processed reaction product.

16 Claims, No Drawings

PROCESSED PRODUCT FOR SKIN AND HAIR TREATMENT

RELATED APPLICATION

This application is a continuation-in-part of the parent application U.S. Ser. No. 184,839, filed Jan. 21, 1994, now abandoned, and entitled Binary And Tertiary Phase Multicomponent, Health, Skin And Hair Treatment Systems And Process For Making And Methods Of Use Thereof, the entire disclosure of which is hereby incorporated by reference.

BACKGROUND OF THE INVENTION

1. Field of the Invention

This invention relates to skin and hair treatment admixtures and compositions having the capacity to promote protection and healing of skin surfaces and the healthy growth of hair on skin surfaces.

2. Background of the Invention

Researchers in the prior art have indicated at least for the last several years that fish oils have been contain certain components, including vitamins A and D and others not clearly identified themselves, which can significantly reduce blood clotting, and make platelets formed internally less likely to stick together to themselves and to blood vessels in the body; thereby lessening the chance of heart attack due to coronary artery clot. It has also been indicated that fish oil might also prevent hardening of the arteries, in that it appeared to indicate in testing that it might be more effective than polyunsaturated vegetable oils in lowering triglyceride levels in the blood. Researchers have speculated that this was why Eskimos and the Japanese, whose diets have been found to include very large amounts of fatty fish, have often been found to have a lower incidence of cardiovascular disease. What has often been expressed in the prior art as being uncertain, is whether fish oil by itself provided all the health benefits of fish, or whether other elements in the fish, or the human ingesting the fish or its oil (fatty acid) component, worked in some combination to bring about positive health benefits.

One such specific study of the health of Eskimos in Greenland, who consume large amounts of fat yet have extremely low death rates from heart disease, indicated that at least one reason for such general health reports was the fact that the Eskimo diet included consumption of large amounts of fish of several diverse species which were rich in omega-3 fatty acids. It was found in this study that if large amounts of fish were consumed for a long period, that the fish oils appeared to thin the blood, lower cholesterol, reduce inflammatory reactions, lessen the risk of arteriosclerosis and protect against colon cancer.

Cod have been found to be one of the most important food fishes for human beings. These fish live in the northern waters of the Atlantic and Pacific oceans. They produce eggs in the depth of the ocean in the late winter and early spring. The eggs of most species of cod fish rise to the surface to become part of the plankton, the mass of small, drifting plant and animal life of the sea. Mature cod eat small fish, squid and shellfish (crabs and shrimp). Atlantic cod have been found to eat almost anything else it finds, including rocks and shells. The physiology of the Cod's gastrointestinal system reveals that powerful juices in the stomach of the fish digest food or sea life that may be growing on an object; the cod then expel what is found to be undigestible. The Cod's diverse and mysterious diet and digestive system have raised many questions as to possible values of cod-liver oil.

This substance is a yellow, fishy smelling oil obtained from the livers of codfish. The liver in cod functions somewhat similar to the human organ, its manifold functions including the storage and filtration of blood, secretion of bile for digestion, excretion of diverse substances formed elsewhere in the organism and numerous metabolic functions. Cod-liver oil has been found to contain large amounts of vitamins A and D, and at one time many people ingested this oil to protect against vitamin A and D deficiencies. However, over the last number of years, cod-liver oil itself has been found to be rarely used, or, when so used, to be taken in the form of capsules, which have been found to possibly limit the positive effects of this oil. Therefore, the question has been raised, as to how to package deliver, or combine this valuable oil in such a way as to deliver older as well as newly-discovered, possible benefits to humans and other animals.

Additionally of the many benefits, some of which may be yet undiscovered, which are attributed to vitamins A and D, each of which is found in cod-liver oil; it has been noted that:

Vitamin A (retinol): helps maintain skin, eyes, urinary tract; and lining of the nervous, respiratory and digestive systems; and is needed for healthy bones and teeth; and that Vitamin D: is essential for calcium and phosphorous metabolism; that it helps prevent 'rickets' in humans, that the $D_3$ form occurs in the tissues of animals including humans, and is called the 'sunshine vitamin' because it forms in the skin when the body is exposed to sunlight; and is converted by the body into an active form which is unique in functioning not only as a vitamin, but as a "chemical messenger" or "hormone".

Additionally, it has been found that vitamin A can aid in treatment of many eye disorders (including prevention of night blindness and formation of visual purple in the eye), in helping form and maintain healthy mucous membranes (as well as healthy skin and hair), in building resistance to respiratory infections, and in treating acne, impetigo, boils, carbuncles, and open ulcers when applied externally. Questions have also been raised and some evidence suggested that other benefits of vitamin A could include controlling glaucoma, buffering against cancer, guarding as a part of a bodily, internal defense mechanism against effects of smog and pollution or other environmental toxicity, cushioning against stress, enhancing and speeding healing, helping in removing age spots, fighting infections, fighting skin diseases and shortening the duration of some illnesses.

Vitamin A has also been found to be essential for normal function of the retina, in combining with red pigment of retina (opsin) to form rhodopsin (necessary for sight in partial darkness), in acting as a co-factor in enzyme systems; and (as in part indicated earlier) its necessity for growth of bone, testicular functions, ovarian function, embryonic development, regulation of growth and differentiation of tissues.

It has, therefore, become an important concern to find new and better ways and systems for better delivery and enhancement of vitamins A and D in the body, utilizing its discovered benefits more effectively and finding new uses and benefits for these vitamins and related delivery means or substances carrying these vitamins, for use in the body and on skin and mucosal surfaces.

Additionally, it has been found that aging reduces the skin's ability to synthesize vitamin D, the elderly tend to go in the sun less (losing this potential source of vitamin D activation), and they absorb less of the vitamin D they consume. As indicated in part earlier, vitamin D deficiency can lead to poor calcium absorption and increased bone loss, and some studies have suggested that 30–40% of elderly people who sustain hip fractures or bad recurrent bruising are deficient in vitamin D. The adequate intake of this vitamin has been linked in having at least a modest effect in lowering the risk of colon cancer, and possibly cancers of the prostate and breast. This, also, emphasizes the importance of developing better delivery means for these vitamins, to obtain the benefits of vitamins A and D, and other valuable components of cod liver oil.

Iodine (I) has been used in medicine over the years as an external, and/or topical antiseptic, both as the free element and in the compound iodoform ($HI_3$).

Iodine is not an abundant element, but has been found to be widely distributed in nature, its salts being found in rocks, soils, seawater and animal and plant tissue. Iodine salts have also, importantly, been found in relatively high concentrations in cod liver oil.

Iodine has been found to be needed in the human body, and deficiency of this element leads to the disease known as 'goiter' (swelling in the neck). As a normal constituent of blood plasma, protein-bound Iodine has a concentration of from about 3.5 to about 8.0 mg/dl.

As indicated in part, iodides are valuable medicines. For example, the antiseptic, tincture of iodine, is a solution of iodine in alcohol.

Iodine has been found to be part of a substance called thyroxine, a hormone produced by the thyroid gland which controls the body's rate of physical and mental development.

It has been found to dissolve only slightly in pure water, but to dissolve more easily if the water contains an iodide, or salt of iodine. The iodide and iodine combine to form polyiodides, which are able to dissolve.

Since the mid-1800's, iodine compounds have been used for what has been found to be their antibacterial properties, possessing a broad spectrum of activity against vegetative and sporulated bacteria, fungi, viruses, protozoa and yeast organisms.

Organic iodine products have been made available as alcohol tinctures or aqueous solutions with molecular iodine in concentrations of 2% to 7%. These iodine substances have been found to stain tissues and have a characteristic odor. Additionally, these substances have been found to be irritating and to potentiate infection if used at stock concentrations. It had previously, therefore, in the art been found that only dilute concentrations of 0.1% to 1% aqueous iodine were acceptable for use on exposed tissues.

Iodophors have been known in the art as products in which iodine were complexed with surfactants or polymers. Povidone-iodine (PVP-I) has been found to be a water-soluble, strongly acidic (pH 3.2) iodophor produced by combining molecular iodine with polyvinylpyrrolidone. Iodophors have been found to be essentially odorless, with less staining being associated with its use. Most commercial povidone-iodine products contain 90% water, 8.5% polyvinylpyrrolidone and only 1% iodine. An iodine has been found in this substance to be complexed to polyvinylpyrrolidone by a loose ionic bond, with an equilibrium being found to exist between povidone-bound iodine and free iodine, thus resulting in a constant release of free iodine until the iodine is depleted. It has been postulated in the art that this might account for povidone-iodine's residual effect of some 4 to 8 hours, as the presence of free iodine ($I_2$) had been found in the art to be directly responsible for the bactericidal effects of iodinated products, the rapidity of bacterial destruction being found proportional to the concentration of free iodine.

Polyvinylpyrrolidone has been found to be a high-molecular weight flexible polymer, having no inherent antibacterial activity itself. It has been said to have an affinity for cell membranes and aid in efficient delivery of free iodine directly to the active site.

Previous studies combined with in vitro data have recommended operational ranges of only 0.1% to 1% PVP-I as a wound lavage solution in that previous to the present invention PVP-I had been associated with some toxicity owing to it acidic pH level and the systemic absorption of iodine. These effects were previously found to be most pronounced when large wounds, body cavities or mucosal surfaces were irrigated.

Additionally, polyhydroxydine is another iodophor found to exist in the art, similar to PVP-I, reported to have antibacterial activity and the ability to enhance wound healing.

Povidone-iodine (PVP-I) is known in the art as a complex which is produced by reacting iodine with the polymer povidone, which as been found, when so complexed, to slowly release iodine. PVP-I occurs in the art as a yellowish brown, amorphous powder in its original reaction composition state; and has been known generally in the art as being used as a topical anti-infective.

When PVP-I is able to be delivered in an acceptable, non-allergic, non-injurious form to an area needing treatment in the body, it is known in the art that this compound, perhaps more than any other antiseptic preparation, is capable of killing all classes of pathogens encountered in various types of infections including gram-positive and gram-negative bacteria (including antibiotic resistant strains and mycobacteria), fungi/yeasts, viruses and protozoa. PVP-I is one of the few microbicides having such a broad spectrum of activity. It has been found that most bacteria are killed in 15 to 30 seconds of application of PVP-I in vitro. It has also been found that microbicidal activity is retained, to some extent in the absence of other conditions or variables such as less effective delivery means; but only in the presence of moderate quantities of blood, pus, mucosal secretions and soap and water, in vitro.

One source of povidone-iodine known in the art, among others, is BETADINE®. "BETADINE"® is a trademark for preparations of povidone-iodine, produced and manufactured by The Purdue Frederick Company of Norwalk, Conn. which is used in relation to some 23 microbicide-product forms. The BETADINE® mark is used in association with microbicide aerosol spray, antiseptic gauze, antiseptic lubricating gel, first-aid cream, vaginal health aids, microbicide ointments, mouthwash/gargle products, perianal health aids, skin cleansers, shampoo products, surgical and antiseptic scrub swab aids and swab sticks, sponge brush products, viscous formula antiseptic gauze pads and whirlpool concentrates among other products.

Some of the warnings appearing in association with BETADINE® products referenced above, which are relevant in consideration of the prior art is that these products are contraindicated for internal use or use in the eyes. Additionally, although some BETADINE® products can be used in association with mucosal surfaces such as vaginal suppositories or in douche applications, it is warned that only limited use should be made of products for these purposes and that such use can be associated with severe irritation and allergic reaction, and pelvic inflammatory disease, a serious infection of the reproductive system. Also, these products are contraindicated and should not be used for application in or treatment of ears, mouth, face or head; with regard to which injury has occurred during such use. Therefore, the development of a product or composition which can effectively complex and deliver Iodine or povidone-iodine compound in a form more acceptable and non-injurious to the referenced internal, eye, ear, face and head areas, and further provision of better treatment and health benefits to these areas has continued in the art to be a long-standing need. An improved delivery system, such as the present composition for complexing delivering components known respectively to be microbicidal and/or health-enhancing, will supply and deliver such components in a physiologically and immunologically acceptable and preferable form such that respective components will provide their known positive health effects and interface with each other to concentrate and improve these positive health effects.

Mineral oil is a clear, colorless, oily liquid with almost no taste or color. It has been used in the past in medicinal and cosmetic preparations such as laxatives and hair tonics. It has also been used as a diluent or dissolver in the manufacture of plastics, and as a lubricant in industrial operations.

Lipids are one of a large group of oily or fatty substances which have been found to be essential for good health. Lipids, carbohydrates and proteins are the classes of compounds present in all living things. Lipids vary more in composition than any other family of biological compounds. It has been set forth that the only feature that is common to all lipids is their poor solubility in water. As waxes, lipids have been found as coatings on leaves and the feathers of birds. In the body lipids have been found to be used for energy, insulation and protection of inner organs. Additionally, lipids have been found in many cell membranes, including the brain and nerves. The fat-soluble vitamins A and D, vitamins E and K, certain hormones and cholesterol (asteroid) have been found to be lipids. Foods which have been found to be rich in lipids have included egg yolks, liver and embryos of grains and other cereals.

Many kinds of organisms store food in lipid form. In animals including humans, it has been found that the bone marrow, tissues beneath the skin and in the intestines, and tissue surrounding body organs in animals consist mostly of stored lipids. Lipids are vital to animals and plants in many ways, constituting a concentrated source of food energy, yielding twice as many calories as an equal weight of protein or carbohydrate.

Certain lipids have been found to form an essential part of the membranes that enclose and protect every living cell; and similar membranes have been found to surround all intracellular components or bodies within the cell so that each such cell body can do its job (such as mitochondria in metabolism and production of energy), without unwanted interference from other cell bodies (such as rough endoplasmic reticulum in synthesizing protein). Lipids have also been found to be valuable as solvents or dissolving substances for vitamins A, D, E and K, which do not dissolve in water.

Steroids as lipids make up an important part of living things. Many animal hormones (as earlier mentioned in part), including the sex hormones and those produced by the cortex or outer part of the adrenal glands, are steroids, in addition to cholesterol found in the membranes of animal cells.

The presence of lipids in the present invention in the form of iodinated cod liver oil, complexed in an aqueous iodine/PVP-I, mineral oil-fatty acid delivery system provide an improved affinity for cell membranes and aid in efficient delivery of free iodine, and vitamins A and D, directly to the targeted treatment area. This, therefore, helps to solve a number of problems that have existed in the art.

In the past it has been found by researchers that when light or other electromagnetic waves strike matter, it behaves as if it were individual particles of energy instead of continuous waves These particles were named "photons" or "quanta", and were found to travel at the speed of light. This idea of photons was considered essential to the quantum theory in physics, originally resulting from experiments conducted by Max Planck in 1900 showing that a photon's energy was proportional to the frequency of its light.

An electromagnetic force has been defined in the art as acting between all particles carrying an electric charge, and is seen in action in all the phenomena of electricity and magnetism, in light and in radio waves. It is known to control the motions of the negative electrons around the positive-nucleus of the atom and is thus the source of all atomic behavior. Electromagnetic force is attractive between oppositely charged particles, pulling them together, and repulsive between similarly charged particles, pushing them apart. This effect has been found to be proportional to the product of the two charges involved and it stretches out from a charge to infinity decreasing as the inverse square of the distance from the charge in a similar way to the gravitational force.

The manner in which the electromagnetic force has been found to act is described in a theory known as quantum electrodynamics, abbreviated in the art as QED, which sets forth that each particle is surrounded by a cloud of photons, the packets of energy without mass such as are present in light. The particle is seen as constantly lobbing out these photons and then catching them again. If a photon meets another particle, an interaction takes place (such as a pulling together if the particles are oppositely charged); and via the photon a particle passes a message to the other particle. A photon cloud has been found under current theory to be the most dense near the particle, and becoming more thin, or thinning when moving out from the particle to infinity. This explains in the art how the strength of the electromagnetic interaction falls off with distance.

Quantum electrodynamics has proven to be a highly successful theory in the art. It has been found subject to testing because, if charged particles have a photon cloud, this will slightly modify their properties. These slight changes have been measured and found to agree with the predictions of QED theory to an accuracy of a few parts in a million, according to the *Encyclopedia of Science and Inventions*, "Particle Physics", H. S. Suttman, Inc., Copyright, 1983. The QED theory was developed in the art originally to explain a comparatively small range of occurring phenomena, but has been found to work perfectly in predicting the effect of the electromagnetic force, whether it involves distances as small as a thousandth of a millionth of a millionth of a centimeter, as for that deep inside a charged particle, or out to distances as large as a million miles.

Among the many applications of QED in the art, it has been found that exposure to a photon component can assist in breaking down a compound or diatomic molecule to the free form of a desired substance, and in providing a source of energy to assist in affecting molecular attraction so as to change the properties of or chemically change, a compound or mixture.

One vivid example of this in the art is the photochemistry of photosynthesis, initiated by the excitation of chlorophyll by light, and the chemical synthesis of carbohydrates (sugars, starches and cellulose) performed in the cells of plants, the necessary energy being supplied by sunlight.

Photosynthesis is the most important natural photochemical reaction. Chemical changes due to radiation of light photons are also basic to photography, and high-energy radiation is additionally able to initiate cross-linking of polymers and synthesis of alkyl halides (gamma radiation). Degradation reactions; the breakdown of complex organic structures to simpler compounds by the influence of bacteria, accelerated by oxygen and sunlight; also, therefore, occur as a result of the ionizing effect of short-wave radiation. Ultraviolet radiation catalyzes the formation of photochemical smog from nitrogen oxides and hydrocarbon air contaminants; and has also been found in the art to initiate photolytic decomposition of ketene and accelerate formation of vitamin D in milk.

In a publication entitled "Sunlight, Ultraviolet Radiation and the Skin", from the National Institutes of Health Consensus Development Conference Statement, Vol. 7, No. 8, May 8–10, 1989; it sets forth, among a number of other findings on this subject, that the exposure of living skin tissue to ultraviolet B sunlight (UVB: 290 to 320 nm. on wavelength spectrum) is essential for the endogenous production of Vitamin $D_3$. This relationship of sunshine to vitamin $D_3$, as indicated in part earlier herein, and the normal growth and development of the skeleton are well known in the art. It is also reported that exposure of skin to ultraviolet radiation through sunlight (UVR), in the region of 290 to 315 nm. is essential for the formation of vitamin $D_3$ in the epidermis of skin tissue. It is also noted that numerous systemic medications may augment UVR susceptibility; and it has been found that increased UVR damage may occur with the use of oral antibiotics, antihypertensives, psoralens, immunosuppressive agents, nonsteroidal anti-inflammatory drugs and many other agents. Additionally, it has been found in the art that a wide range and number of topical medications and industrial chemicals may increase the susceptibility of damage to the skin by sunlight. Some of these medications and chemicals include topical psoralens, tretinoin, and other photosensitizing and depigmenting agents.

Ultraviolet radiation in sunlight has been found to be critical for vitamin D synthesis in the skin, as indicated. However, UVR has also been found to produce a wide variety of pathologic effects, including sunburn, pigmentary change, immunologic alterations, and neoplasia. A noted collection or gathering of structural alterations, histological changes, of the epidermis, the dermal-epidermal junction, and the dermis of integumentary tissues has been found to be characteristic in diagnosis of photo damage.

These finds, therefore, indicate the need in the art of a topical composition which will heal skin tissue and promote protection from ultraviolet radiation from the sun while augmenting the valuable health benefits provided by the sun in vitamin $D_3$ activation and formation in epidermal layers of the skin.

Various types of cosmetic hair growth compositions or topical skin compositions have been known in the art. Typical of these inventions are U.S. Pat. Nos. 5,211,942; 5,183,817; 5,137,718; 5,041,439; 5,032,382; 4,978,527; 4,954,341; 4,912,111; 4,584,192; 4,401,651 and 4,393,043; issued respectively to Deppert, Bazzano, Gillespie, Kasting, Grollier, Brink, Nakamura, Sank, Dell, Knutson and Koulbanis. Copies of the patents cited were enclosed with the parent application pursuant to 37 CFR §§1.97–1.99.

The Gillespie '718 patent reference discloses a topical antimicrobial cream, essentially comprising a povidone-iodine complex and hydroxyethyl cellulose component, a water soluble emollient such as glycerin, a water soluble surfactant such as nonyphenoxy-polyethanol such as IGEPAL CO-660, and water to form a homogenious solution having a gel-like consistency and clearly not resulting in, or functioning as a system having, stratification into separate co-existing layers.

The Kasting '439 reference discloses a topical hair-growth composition comprising a defined hydroxy imunopyrimidine compound, a solvent such as water or ethanol and a penetration-enhancing carrier consisting of a polar solvent such as 1,2-propanediol is defined combination and ratio with a polar lipid compound which is isocetyl alcohol.

The Grollier '382 reference discloses a light-stable screening cosmetic composition for protecting the skin from UV radiation, comprising a defined weight of bixin compound and a weight percentage of lipid-soluble screening agents including 3-benzylidene-dl-camphor and benzophenome derivatives in a cosmetic vehicle having a fatty phase component. Bixin utilized therein takes the form of an oily extract of annatto containing 0.1% by weight of bixin.

The Brink '527 patent reference discloses a dermatological film-forming emulsion having a film-forming coploymer phase having three monomers, where the first monamer is a monomeric acrylic or methacrylic acid ester of an alkyl alcohol containing a single hydroxyl, the second monamer is a further defined monmeric methacrylic acid ester of an alkyl alcohol, and the third monamer is an N-vinyl lactam and a monamer containing a polyether functionality. The Brink emulsion further comprises a defined percentage of iodine based on total emulsion weight, an emulsifying agent, and a defined percentage by weight of water.

The Nakamura '341 reference is perhaps an example of what appears to be a number of references in the art utilizing an ammonium salt in a hair cosmetic composition. The Nakamura composition comprises a defined percentage by weight of at least one tailored quaternary ammonium salt, in combination by weight and ratio to a defined phosphate.

The Sank '111 reference discloses the use of Minoxidil for wound healing, and the Bazzano '817 patent reference discloses combinations of Retinoids such as Vitamin A acid and Minoxidil-type compounds for hair growth.

The Dell '192 reference discloses a film-forming skin composition comprising three monomers, where the first monomer is an alkyl alcohol containing a single hydroxyl, selected from a group consisting of n-butyl acrylate, isoocytl acrylate and lauryl methylacrylate, the second nomamer is a methacrylic acid ester of an alkyl alcohol such as methanol, ethanol or 1-propanol, selected from a group including methyl methacrylate and n-butyl methacrylate; and the third monamer is an N-vinyl lactam such as N-vinylpyrrolidone, for complexing iodine. The composition further includes an amount of an antimicrobial agent such as iodine of 0.1 to 15% by weight of the copolymer composition.

The Knutson '651 patent reference discloses a wound-healing skin composition containing povidone-iodine, comprising an antimicrobial ointment constituting an admixture of 20 parts by weight of ordinary granulated sugar, 5 parts by weight Betadine® ointment and 2 parts by weight of Betadine® solution.

The Deppert '942 reference discloses in its summary in the Official Gazette, Halide Containing Quaternary Ammonium Salts as hair conditioning agents.

The Koulbanis '043 reference discloses a cosmetic composition containing a solution of 0.5 to 20% by weight essential fatty acid such as Vitamin F and jojoba oil and arachidonic acid.

Additionally, the Chaussee, N'Guyen and DuBois patent references have been brought to the applicant's attention.

Though it appears that some use of mineral oil, cod liver oil and povidone-iodine are taught in Chaussee as alternative use substances; there proportions, method of entering the substance and ultimate delivery means in combination with other substances is substantially different than as set forth in the present inventive composition. Additionally, Chaussee does not specifically tie in whatever means employed to make that substance, to its final product, as done in the present invention. One skilled in the art could pursue a number of different processes to arrive at Chaussee's final product; whereas in the present invention, the novel process of making the product and the product composition itself are each novelly and specifically tied to one another. No other process of making the present invention is acceptable or consistent with the teaching of the present hair and skin composition. In the present invention, both the process and the final product composition are distinguishable from, and not obvious in view of, Chaussee.

It would appear that the N'Guyen patent reference discloses and claims a cosmetic composition comprising what it terms a cosmetically acceptable fatty body, an antioxidant system containing very different substances from the present invention; including tocopherol, caffeic acid, an ascorbyl ester of an aliphatic acid, a complexing agent such as ethylenediamine tetracetic acid or citric acid and a thiol such as N-acetyl cysteine. The "acceptable fatty body", as set forth in N'Guyen, can be a food composition such as edible oils or margarine; and the cosmetic composition of N'Guyen can be in the form of a cream for the purpose of protecting against oxidation of skin lipids. However, the complexing or delivery system by which N'Guyen's margarine is introduced, together with the method of introducing substances, appears materially different; with no suggestion being found in N'Guyen's disclosure that mineral oil, cod liver oil, povidone-iodine or other components including other iodine complexes or photon light component can be utilized as in the case of the present invention to produce an iodinated cod liver oil complex in a matrix comprising a plurality of fluid phase levels which then may be recombined synergistically prior to therapeutic application; or with regard to the disclosed uses of the present invention.

It would appear that one object of the DuBois teaching is to provide a cosmetic product for skin care containing natural emollients used in association with paraffin hydrocarbons (i.e., saturated hydrocarbons of the formula $C_nH_{2n}+2$, i e., "alcanes") and lecithin. However, DuBois discloses and claims an emulsion in aqueous phase consisting specifically of water and an extract of hydro-dispersible lecithin enriched in phosphatidylcholine in a proportion between 0.01% and 5% of the weight of the water and an oil phase consisting of paraffin hydrocarbons that are oily or solid and liposoluble lecithin, with the oily phase constituting between 5% to 90% by weight of the whole. There appears to be no suggestion in the DuBois teaching, that an oil phase be complexed with other ingredients found in the present invention and be processed by any method (especially involving photo reaction) akin or related to what is disclosed in the present invention with regard to binary or tertiary phase processes involving the important photon component and process of nucleophilic substitution of cod liver oil organic compound, and production, which takes place as a result thereof to produce the composition of the present invention.

It is therefore submitted that one skilled in the cosmetic art or that of hair treatment or the healing of skin problems, would not be motivated to combine the Chaussee, N'Guyen or DuBois references, or any of the other references found in the prior art, to achieve the present invention. Even, if it were assumed, that the three skin care emulsions or compositions disclosed or taught in Chaussee, N'Guyen and DuBois suggested a possible combination of their components, which they do not, one still would not have the teachings of the present invention.

None of the references specifically illustrate or teach the present invention. Nor is the present invention obvious in view of any of the prior art references listed herein. The chemical components and relationships there-between are significantly different in the present invention, as is the specific tied in process of the invention of combining the present components novelly to produce the final product composition of the invention. Additionally, concurrent phase level relationships, which function in relationship to one another in the final product are not present in the relevant prior art. All of the prior art heretofore known suffer from a number of important disadvantages:

(a) None of the prior art substances utilize a nucleophilic reaction between Iodide ions supplied from an Iodine/Povidone-Iodine complex, and a Cod Liver Oil—organic compound, which is activated and catalyzed by a photon component from sunlight and hastened by dilution and supply components comprising mineral oil/water and Red Iodine/Povidone-Iodine components to dilute the Iodine components and provide free iodide ions to thereby substitute these ions for alkyl functional groups on the Cod Liver Oil compound; to produce a final processed iodinated cod liver oil product in a matrix having at least binary fluid phase levels; which, then, upon being mixed together, provide further synergistic properties facilitating stronger healing and treatment properties prior to and upon topical or systemic application.

(b) The prior art substances do not have the substantial capacity to be adequately utilized to promote healing of skin disorders, infections, insults and wounds together with promoting the healthy revitalization and growth of hair, hair follicles and fingernails: or to consistently have the capacity to reach epidermal, subdermal, dermal, duct and nerve root regions associated with skin and mucosal cell and tissue regions.

(c) The prior art substances are not designed to promote adequate temperature stability on skin and mucosal surfaces while providing protection against UV radiation, light rays and promoting even, consistent, noninflammatory, non-peeling suntan thereon.

(d) The prior art substances are additionally not designed to concurrently provide protection against insect and arthropod infestation while also promoting the healing of bites, stings and infection created by components of associated sting elements, and head/appendage elements left inserted in layers of human and animal skin tissue.

(e) It is a further disadvantage of the prior art substances that most all are moderately to substantially toxic if orally ingested or administered in substantial doses topically on the skin surface or by absorption or ingestion to deeper layers of the skin or mucosal surfaces.

(f) It is a further disadvantage, that prior art substances cannot be concurrently administered in therapeutic doses to mucosal, sublingual, subpharyngeal, bronchial and other areas of the oral cavity, throat, trachea and esophagus, or to areas of the anus, bowel, genitals, auditory canal or sinus areas.

(g) A further disadvantage of prior art inventions is their substantial inability to consistently work well, or work at all, in association with, or when used concurrently with, other oral, internal or topical healing or antimicrobial agents administered to animals and humans.

(h) Prior art substances also fail to consistently or adequately, concurrently promote soft, healthy skin surfaces while significantly helping to remove signs of aging wrinkles, warts, blemishes or other insults or irregular growth patterns of the surfaces of skin and mucosal tissue, as the present invention does.

(i) Prior art substances also fail to provide concurrent relief for muscle, joint and spinal pain and tension, and circulatory problems in these regions.

(j) Yet a further disadvantage is the lack of the substantial, or concurrent capacity to clean and provide protection associated with good health to animate and in animate surfaces, or fomites, as the present invention does.

One of the central objects of the processed product of the present invention is to provide a productive complex of admixed components which will both, provide a vehicle for and enable efficient and timely iodination by nucleophilic substitution of alkyl functional groups on a cod liver oil component, and provide a transfer complex through remixing of the product's fluid levels prior to application, to allow synergistic reassociation of the fluid levels, enhancing the properties and effects of each of its product reaction components, and their ability to be delivered to, and reach targeted treatment areas.

Another principal object of the invention is to provide a processed product which is produced by utilizing a nucleophilic reaction between Iodide ions, diluted from and supplied by an Iodine/Povidone Iodine complex, and Cod Liver Oil; energetically activated by natural sunlight or substantially equivalent artificial light, and photo-reaction with Cod Liver Oil; and assisted and hastened in the dilution of iodide ions by fluid-dilution means comprising mineral oil and water; to produce a processed product with a plurality of fluid stage levels comprising respective reaction product components; which, after sun or a light exposure, are remixed to provide enhanced and synergistic chemical property effects to one another and provide a more effective transfer medium or complex for delivering components of the processed product to skin and hair areas targeted for treatment.

A further object of the present invention is to provide a specifically and critically linked product by process comprising the presence of lipids in the form of iodinated cod liver oil, complexed in an aqueous Iodine/PVP-I, mineral oil-fatty acid delivery system to provide an improved affinity for cell membranes (also containing lipids), and aid in the efficient and more timely delivery of free iodine, vitamins A and D, and other health benefits of cod liver oil, directly to the targeted treatment areas, both internally and externally in humans and animals, thus improving means of delivery to these areas and solving associated long-term needs in the prior art.

Another, object of the present invention is to provide a consistently effective, therapeutic composition system which is concurrently effective, by varying mode of delivery and therapeutic doses, in facilitating healing of a diverse range of skin and mucosal problems, disorders, abnormal growth and infections while promoting productive growth of hair or fur; promoting nontoxic, noninflammatory, topical fluid temperature stability on skin surfaces while protecting against damaging ultraviolet rays and facilitating consistent overall, attractive, non-peeling suntan development; and repelling from skin, hair and fur surfaces many diverse species of arthropods and insects while facilitating healing of their prior damaging effects, including expulsion of attached or embedded insect/arthropod bite, attachment or sting elements, and healing of their associated wounds or infection.

An additional object of the present invention is to provide a mixable binary or ternary fluid composition system which is cost-effective in preparing, which has the capacity as a topically or internally administered medicine to reach and affect deeper layers of skin tissue, mucosal tissue and tissue associated with various body orifices, including nerve endings, in a substantially nontoxic manner, and to be easily utilized with other forms of therapeutic treatment and medicine regarding these tissues, associated component cells and surfaces, in both human and veterinary medical applications.

It is yet a further object of the present invention to provide a binary and tertiary fluid composition system where the individual layers when mixed and applied act to facilitate one another functionally in softening and cleansing skin surfaces; and relieving muscle, joint and spinal oriented pain, tension and circulatory problems, while having the concurrent capacity to provide microbialcidal and microbialstatic protection to both animate and inanimate surfaces.

SUMMARY OF THE INVENTION

The foregoing and other objects can be achieved with the present invention which is a product which is specifically and critically linked to its process of production. This processed product comprises an Iodine means, such as a tincture of iodine solution/povidone iodine complex, which can provide a source of diatomic iodine and iodide ions by virtue of the presence of diatomic iodine and its properties in tending to form, or being more easily diluted to form, iodide ions; a fluid means for diluting the iodine means, such as mineral oil, water and/or alcohol, so that the necessary iodide ions can be more easily made available from the Iodine means for nucleophilic substitution of available alkyl functional groups in the admixed components; a cod liver oil, organic compound, component having a plurality of potentially available alkyl functional groups and lending itself more easily by virtue of its properties to nucleophilic substitution of its alkyl functional groups; and a photon light energy source component, preferably and critically provided by natural, ambient sunlight, for providing increased energy activity or photo-catalytic qualities so that the light reacts with the diatomic iodine in the iodine means, working together with the dilution effects of the fluid means, to break down the iodine means to provide more iodide ions more quickly from the iodide means, making them available more rapidly consistently, and economically, for nucleophilic substitution on the available alkyl functional groups of the cod liver oil component, the iodide ions generated acting as an effective nucleophile to complete for and become bonded to these alkyl groups. In the critically linked process of producing the processed product of the present invention, the Iodine means, containing preferably tincture of red iodine solution and povidone-iodine fluid complex components, is admixed with the cod liver oil component; and, then, exposed to directed, ambient natural sunlight so that the admixed components having a generally dark coloration, irreversibly change to a substantially white/clear product having a pH of about 6.5 to about 6.8, and having at least binary fluid levels. The fluid levels are then remixed prior to therapeutic application for the treatment of hair and skin problems so that the remaining reaction product and properties of each fluid level of the processed product are mixed with each other again for synergistic chemical property enhancement prior to application on targeted areas for treatment.

Principal uses of the present invention include multi-diverse applications to skin and mucosal layers and hair to inhance growth, healing or protection; and a number of applications involving interior portions of the body, as well as animate, inanimate surfaces, to serve therapeutic and other purposes.

DETAILED DESCRIPTION OF THE PREFERRED EMBODIMENTS OF THE INVENTION

The processed product of the present invention provides the production of a multiple fluid phase product specifically and critically tied to a process of producing this product for use, among many other uses, in the treatment of hair, skin, mucosal membrane, and internal joint and muscle problems.

The final product of the present method comes to exist concurrently as a binary or tertiary (three-level) fluid phase-level composition system, having two (2) or three (3) discernable fluid layers, which, when mixed or remixed prior to therapeutic-dose application, function synergistically to enhance each other functionally on the surface or targeted area or region of a human or animal body to which it is applied, facilitating further reaction and function (and/or physical or chemical properties) in relation to cellular or molecular layers or components of the skin and/or mucosa.

In a basic preferred embodiment of the invention, a critically-tied process for producing the novel hair and skin treatment composition as a processed product, comprises the initial step of adding to a substantially transparent container the following admixed components:

(a) A cod or equivalent fish liver oil fluid, (b) a povidone-iodine fluid complex, (c) an iodine fluid or solution, preferably in tincture form (d) a margarine or fatty oil component or compound, (e) a water component, and (f) a mineral oil or fluid petroleum equivalent derivative.

The adding or admixing of these components together causes a concurrent binary phase (two-level) or tertiary phase (three-level) fluid composition admixture to be formed, having bottom and top volumes, or bottom, middle and top volumes, adjoining one another, with the bottom layer expressing or showing a very dark coloration in appearance.

The vibrating or shaking and thorough mixing of these components; and, then, exposing these admixed components in their single mixed fluid phase condition, to photon-light attack and absorption, preferably from bombardment of the rays from natural sunlight; then facilitates and causes a reaction to take place in the mixed fluid, causing the components in the container to produce a first layer oriented towards the bottom of the container which then, upon exposure to the sunlight, changes in coloration from the earlier dark-colored bottom layer, to a clear, semi-transparent colored appearance. Exposure of the admixed components to the natural sunlight, or substantially equivalent artificial light source is a critical part of producing the processed product of the present invention.

In a preferred embodiment of the invention, the adding step includes utilization of from about 0.1 to about 4.00% by weight of cod or fish liver oil, or derivative or constituent of this; from about 0.2 to about 12.0% by weight of total iodine/povidone-iodine complex utilized (of the total weight of composition); from about 10.0 to about 45.0% by weight of water; and about 40.0 to about 80.0% by weight of mineral oil or fluid petroleum derivative, such as mineral oil, baby oil or derivative or constituent thereof.

The critical component of the present processed product in the exposure of the admixed components to photon-light bombardment should preferably be with the minimal range of time of from about 12.0 minutes to about 15.0 minutes. This time may also preferably extend to as long as about 60 minutes. The preferred reaction of the present invention will start to take place in as little as 10 to 12 seconds, and will become substantially irreversible in nature in about 10 to 15 minutes. Only light having the same photon and quantum characteristics of sunlight would, should such a light source exist and be available, be the only acceptable option or alternative in the present processed product as a light or photon exposure component.

In a preferred embodiment of the invention, a substantially transparent and melt-resistant container containing and housing the admixed components is placed on a generally horizontal surface so that it may be exposed to natural or ambient sunlight on days and at times of a selected day when substantially complete exposure or lumination to a chosen horizontal surface is most advantageous.

Additionally, the container housing the admixed components can be placed on a horizontal surface exposed substantially to the sun's natural lumination; and one to three mirrors, each having at least one substantially flat reflective surface, can then be placed at substantially equivalent spatial distances from adjacent container-wall portions. Each of the mirrors is secured to the sun-exposed horizontal surface so that the reflective surface of the mirror faces the container and is positioned to reflect the sun's light rays onto the container and into the admixed components housed in the container. In a preferred embodiment it was found that the best angle to tilt the reflective surface of each mirror relative to the horizontal was from about 72° to about 78°, but that this preferred angle could vary dependent upon the available sunlight on a given day, the preselected location of the horizontal surface and the time of a given day. One such preferred time of day during a generally sunny, clear day is from about 10:30 a.m. to about 11:00 a.m. on such a day.

Additionally, in a preferred embodiment, the mirrors are spaced and facing a container having vertical half-portions thereof which are mirror images of one another, or having consistently proportional configurational sides about a common axis; with the mirrors being spaced at about 18 inches from the axis of the container, or adjacent wall-portions of this type of container.

In another preferred embodiment of the present invention, an artificial light source is utilized. One such acceptable light source found to essentially approximate a natural sunlight source has been found to be an electrically activated 500 watt halogen flood light bulb. In this embodiment one container, or a plurality of containers, housing the admixed components of the present invention, can be placed in front of this type of artificial light at a distance from this light source of about 12 inches; though different other distances may be employed depending on the conditions of the supporting surface environment, light temperature and heat/temperature capacity of materials utilized in the construction of the container, which may be a such materials as transparent plastic or polymer substances such as those generally housing baby oil or mineral oil to more resistant materials such as PYREX®, laminated or other materials. In utilizing this type of artificial light source, a preferred, irreversible processed product of the present invention can be obtained in a preferred time period of 38 minutes, or from about 10 to 40 minutes depending on environmental or ambient conditions; whereas in utilizing natural sunlight as a photon energy source, the process and product will take ideally closer to 60 minutes.

In a preferred embodiment the container housing the admixed components is rotationally turned within its substantial positional location on a horizontal surface, for more evenly distributed exposure to the available light source, about every 12 to 15 minutes. Additionally, it has been observed in utilizing the present invention, that exposure of the admixed components to preferred light sources brings about an initial process reaction in about 10 to 12 seconds dependent on environmental conditions.

In utilizing the present invention for the uses disclosed, it has been found that natural sunlight as a source of photon energy is preferred over the use of artificial sources of light because natural sunlight provides gamma radiation and other chemical, photon or physical properties which traditional artificial light does not provide; which are otherwise critical for producing the processed product for therapeutic use on targeted skin and hair regions. Artificial light at certain intensities equivalent or greater than the referenced 500 watt flood light have been found to contain ultraviolet radiation approximating that of natural light; and where substantially this general property is desired, it is appropriate for use in the present invention.

The processed product of a preferred embodiment of the invention for producing a binary or tertiary fluid phase, skin and hair treatment composition, constitutes a fluid phase level having diluted dehalohgenated lipid hydrocarbon components and free associated halogen (preferably iodine) components. This phase level volume is clear and semi-transparent in appearance. The product also has a second or additional phase level volume substantially or almost completely constituting a mineral oil component. Preferably this composition is a reaction composition comprising BETADINE®-iodine fluid complex, cod or fish liver oil component, filtered water component, mineral oil component and an absorbed amount, or quantum absorption component- amount, of photon-light energy.

Iodine components occurring and being utilized in the present invention are found to be nucleophilically substituted onto lipid hydrocarbon chains of the cod or fish liver oil component so as to form at least one (1) to three (3) double bond structures (olefin/alkene, alkadienes/dienes/ diolefin or triolefin-structure), per lipid halogenated hydrocarbon per functional molecule.

Additionally, a preferred embodiment of the binary composition of the present processed product of the invention includes the specific utilization of standard cod fish liver oil, a combination of BETADINE® and Red Iodine fluids or tincture solutions thereof, charcoal filtered water and standard mineral oil, or component or equivalent derivative of this oil. In the final unmixed reaction processed-product, after exposure to the sunlight component, the first bottom phase layer of composition is almond, off-white in coloration, and the second layer is clear, semi-transparent in appearance.

In another preferred embodiment of the present invention, the processed product of the present invention is produced and specifically tied to its process of production in making a tenary (or tertiary) phase fluid treatment composition which comprises adding the following components to a preferably, generally transparent or semi-transparent beaker, bottle, reservoir or other housing container:

| (a) | Cod Liver Oil fluid, |
| (b) | Povidone-Iodine fluid complex component (preferably BETADINE ® solution), |
| (c) | Iodine fluid component (preferably tincture or red iodine solution), |
| (d) | Partially to substantially saturated fatty fluid emulsion or oil (preferably margarine compound), |
| (e) | Filtered water component, and |
| (f) | Fluid petroleum derivative, generally clear or colorless in its original state as provided (preferably standard mineral oil). |

These components are added to, and admixed within, a housing container or suitable container means under generally indoor ambient conditions of standard room temperature, pressure and light intensity or light character. Under these conditions the initial admixture of components forms an initial tertiary (three) phase composition having a dark- reddish-brown-black colored bottom volume in the housing container; a yellow-colored middle layer volume oriented over and adjoining the bottom volume; and a reddish-orange colored upper or top layer volume in the container adjacent in spatial position to the middle level volume. This tertiary phase composition constitutes stage one (1) of this preferred embodiment of the present processed product invention.

The added components in the container are then well mixed or vibrated, or shaken, so that they form a generally, overall, brown-dark coloration, single fluid phase. The mixture is then placed in a position to be exposed to photon-light bombardment, preferably from a natural sunlight source, or other source, should this exist, which can substantially approximate or duplicate the quantum component, sunlight photon energy, wavelength and/or intensity or characteristic character of actual natural sunlight. Exposure to sunlight is a critical part of the processed product, or process by product, of the present invention. The mixed components are preferably exposed to the photon-light bombardment where the light can enter from substantially all sides or ambiently available angles of the transparent housing container holding and housing the admixed components, for a period of time for at least about 12 minutes to about 15 minutes at least, to approximately one (1) to four (4) hours, or possibly longer if needed under the specific relevant light and environmental conditions at the time. Additionally, this part of the process can be augmented by placing a mirror or mirror means, or reflective, light intensifying or directing means, at strategic locations around the admixed component-housing container so that a rich source of light and photon energy constituent thereof can thereby reach all or substantially all container locations to impart quantum component photon energy to substantial locations of the mixed components.

It will be appreciated by those skilled in the art that the concepts of the present invention and processed product also encompass the utilization of an artificial or man-made nuclear reaction-generated light or photon energy source, or like reaction in a nuclear reactor, for the photon light energy source component of the present invention.

After exposure of mixed stage one components of the present invention to sunlight or equivalent quantum component, photon-light energy for a required period of time, so that a clear bottom layer is formed in the container, the mixed components break down into redefined, first-bottom, second-middle and third-top phase layers within the housing container. The bottom layer is changed in color, as indicated, from dark, reddish-brown of stage one to clear, semitransparent in appearance (stage 2), and is reduced in volume from the stage one bottom layer. The middle layer is changed in color from yellowish-color of stage one to whitishcolored in appearance in stage two and is increased in volume from the stage one middle layer. The top layer is changed in color from reddish-orange of stage one to almond-off-white color in stage two, and is increased in volume from the stage one top layer.

In testing, utilizing the present invention, it was determined that a critical step in the process and method of deriving the product formulation was exposure of the mixture to sunlight or substantially equivalent artificial light which changed the product color at the bottom phase of the composition from a reddish brown to clear/white or semi-transparent; and converted the Iodine presence in the first stage which could be potentially toxic, to an iodide presence in the second stage which was substantially non-toxic.

In testing concerned with isolating the components involved in the color change and determining the color change mechanism; container type (housing the composition) and position of the container relative to the ground, and angle of the sun was during this testing found not be critical. Exposure to sunlight was, however, found to be a necessary critical component of the process, product and inventive system. Tests showed that two components were minimally and specifically necessary as a part of the invention for reaction to sunlight: Cod Liver Oil and Tincture of Iodine/BETADINE (which contains Iodine). Water and/or mineral oil were found to dilute the Iodine and hasten the action. Both Tincture of Iodine and BETADINE, or solutions of these components, were found separately or individually and/or combined to react with Cod Liver Oil when exposed to direct sunlight, and change color from brown to white/clear. The only samples which did not complete the reaction in a reasonable time contained high concentrations of Iodine/BETADINE which were not diluted with mineral oil/water and Tincture of Iodine/BETADINE alone. These trials contained the following solutions:

| Container Identification | Contents |
| --- | --- |
| A | ¼ cup Baby Oil, 6 drops Iodine |
| B | ¼ cup Baby Oil, 6 drops BETADINE |
| C | ¼ cup Baby Oil, 6 drops Iodine, 6 drops BETADINE |
| D | ¼ cup water, 6 drops Iodine |
| E | ¼ cup water, 6 drops BETADINE |
| F | ¼ cup water, 6 drops Iodine 6 drops BETADINE |
| G | Tincture of Iodine |
| H | BETADINE |
| I | 50% Iodine/Betadine, 50% Cod Liver Oil |

The containers were placed outdoors in the sun and were vigorously shaken periodically, starting just prior to placing the container in the sun. After four hours there was no discernable color change in any of the mixtures, except in container I which had a slight orange tinge. Three drops of Cod Liver Oil were added to all of the containers, except container I, and the containers were shaken again. After one hour of further exposure to the sun the solutions in containers A, B, D, E and F were white/clear in appearance. The solution in container C was light brown to orange in color, and the solution in container one (1) had a very slight orange tinge. The color of solution one (1) changed from dark red to white over a period of four (4) days of exposure to the sun. Therefore, the reaction during this round of testing was pinpointed to that of a reaction between Iodine and Cod Liver Oil caused by exposure to sunlight and timely and more efficiently hastened or exacerbated by Iodine component dilution from what appeared to be elements of water and/or mineral oil.

In reviewing the invention reaction between Cod Liver Oil and Iodine components, it was found, as indicated, that sunlight was an important ingredient and component of the inventive concept and the special utilization involved therein. The basic phenomenon taking place in part of the invention is set forth in part in the prior art and is partially explained in several general chemistry and organic chemistry textbooks. The reaction between an iodine ion (or any other halide ion) and an organic compound such as one having lipid hydrocarbon chains, with available functional groups, which Cod Liver Oil is known to have, is a nucleophilic reaction. These reactions involve the substitution of one functional group, such as an OH group, by another such as a halide or iodide ion. The reactions are ionic/polar reactions involving the attack by a nucleophile, such as an iodide ion, at a carbon atom within an organic molecule.

A functional group attached to the carbon atom is replaced by the iodide ion. This is a competing reaction for the same carbon atom. The nucleophile can undergo displacement or elimination. Therefore, the functional group must be weakly held by the carbon atom for the reaction to proceed at a reasonable rate.

Cod Liver Oil is a mixture of several organic molecules with saturated and unsaturated bonds. As a result, there are amply sufficient functional groups which can be replaced by iodide ions. Tincture of Iodine and BETADINE solutions both contain diatomic iodine and iodide ions. Sunlight is important in the creation of iodide ions from diatomic iodine. This creation of additional iodide ions allows for a much more efficient nucleophilic substitution for alkyl functional groups in the Cod Liver Oil. Iodine has a reddish brown color. As the iodine is broken down by the sunlight to two (2) iodide ions, nucleophilic substitution occurs. In so doing, the color of the solution changes from reddish brown to clear or semitransparent in appearance.

In a preferred embodiment of the present invention method, Cod Liver Oil fluid is selected from a group including oils obtained from the liver of cod fish and related fishes, rich in vitamins A and D, Iodine, and derivatives of these fluids or equivalent synthetic substances.

The halogen fluid complex is selected from a group including halogen/halide fluid complexes, povidone-iodine fluid or solution complexes, BETADINE fluids or tincture solutions, iodine fluid or tincture solutions, including among others Red Iodine Tinctures and equivalent synthetic substances or constituents/derivatives of these substances. Fatty fluid emulsions are selected from a group including margarines, butters, partially to substantially saturated fatty suspension fluids, oils and emulsions, paraffin constituents and derivatives, and equivalent synthetic substances. The water component is selected from a group including charcoal-filtered water solutions and water substantially filtered, purified and cleaned by other, similar processes. Fluid petroleum derivatives are selected from a group including mineral oil fluids and solutions, available baby oil fluids, or equivalent petroleum derivatives or constituents thereof.

In a preferred embodiment of the present invention, the stage two (or second stage) of the treatment system composition comprises a BETADINE tincture or solution component, an iodine tincture or solution component, a filtered water component and a quantum light energy component. In this phase segment of the invention system the fluid has turned clear, semitransparent in appearance, and the composition has reacted or changed so that iodide components exist separate in the fluid and/or have attached as iodide component to lipid hydrocarbon functional groups by substitution as explained herein.

In tests utilizing preferred embodiments of the invention, the following components and amounts, ratios of components and percentage of components utilized in test runs including the following:

|  | Weight (grams) | % | Ratio |
|---|---|---|---|
| (a) Cod Liver Oil | 4.76 g. | 0.90–1.0 | 1.00 |
| (b) BETADINE soln. | 10.0 g. | 1.90–2.0 | 2.10 |
| (c) Red Iodine Soln. | 7.0 g. | 1.30–1.33 | 1.47 |
| (d) Margarine | 28.0 g. | 5.30–5.32 | 5.87 |
| (e) Water | 113.0 g. | 21.45–21.5 | 23.69 |
| (f) Mineral Oil | 364.0 g. | 69.00–69.1 | 76.34 |

|  | Amount (milliliters) | % | Ratio |
|---|---|---|---|
| (a) Cod Liver Oil | 5.0 | .87–.89 | 1.0 |
| (b) BETADINE soln. | 10.0–15.6 | 1.78–2.72 | 2.0–3.13 |
| (c) Red Iodine Soln. | 7.4–12.0 | 1.32–2.10 | 1.5–2.41 |
| (d) Margarine | 30.0 | 5.24–5.33 | 6.0 |
| (e) Water | 120.0 | 20.96–21.34 | 24.0 |
| (f) Mineral Oil | 399.0 | 68.11–69.35 | 78.0 |

|  | Weight (grams) | % | Ratio |
|---|---|---|---|
| (a) Cod Liver Oil | 4.8 | .91 | 1.0 |
| (b) BETADINE soln. | 10.0–14.8 | 1.90–2.70 | 2.08–3.08 |
| (c) Red Iodine soln. | 7.0–12.5 | 1.33–2.28 | 1.45–2.60 |
| (d) Margarine (oil) | 28.0 | 5.10–5.33 | 5.83 |
| (e) Filtered Water | 112.0–125.0 | 21.30–22.76 | 23.31–26.02 |
| (f) Mineral Oil | 364.0 | 69.23–66.29 | 75.76 |

|  | Weight (ounces) | % | Ratio |
|---|---|---|---|
| (a) Cod Liver Oil | .17 | .91 | 1.00 |
| (b) BETADINE soln. | .34 | 1.81 | 2.00 |
| (c) Red Iodine soln. | .25 | 1.33 | 1.47 |
| (d) Margarine | 1.00 | 5.33 | 5.87 |
| (e) Filtered Water | 4.00 | 21.32 | 23.49 |
| (f) Mineral Oil | 13.00 | 69.30 | 76.34 |

|  | Weight (grams) | % | Ratio |
|---|---|---|---|
| (a) Cod Liver Oil | 4.80 | .91 | 1.0 |
| (b) BETADINE soln. | 9.52 | 1.81 | 2.0 |
| (c) Red Iodine Soln. | 7.0 | 1.33 | 1.47 |
| (d) Margarine | 28.00 | 5.33 | 5.87 |
| (e) Filtered Water | 112.00 | 21.32 | 23.49 |
| (f) Mineral Oil | 364.00 | 69.29 | 76.34 |

ADDITIONAL TESTING - RANGE OF VALUES

| Grams | ml. | oz. | % | Ratio |
|---|---|---|---|---|
| 4–5 | 4–6 | .1–.2 | .80–1.5 | 1.0 |
| 9–15 | 9–17 | .3–.4 | 1.00–3.0 | 2.0–3.2 |
| 6–13 | 6–13 | .2–.3 | 1.00–3.0 | 1.4–2.6 |
| 27–29 | 25–35 | .5–2.0 | 4.00–6.0 | 5.0–6.0 |
| 111–126 | 110–130 | 3.0–5.0 | 18.00–25.0 | 23.0–26.2 |
| 360–370 | 380–400 | 10.0–15.0 | 60.0–72.0 | 76.0–78.0 |

A therapeutic dose, utilization, application or administration, as used and/or characterized through the examples of the present invention set forth herein, pertain to the amount and/or mode of delivery, of a nontoxic, noninflammatory nature; and in the appropriate amount to bring about effective treatment, healing or the remedial, curative or preventive purposes desired which are described as being within the scope of uses set forth herein, with respect to the present method, process, system and composition of the present invention.

Additionally, as set forth in this specification and claims, the words or terms: "therapeutic", "average dose" and "therapeutic dose" have been utilized in a manner of definition consistent with traditional sources including Wester's New World Dictionary (1980), Dorland's Illustrated Medical Dictionary (1988) and Bailliere's Comprehensive Veterinary Dictionary (1990) as follows:

"Therapeutic": curative; serving to cure or heal, to preserve health, e.g., "therapeutic amount"; also dealing with "therapeutics", a branch of medicine dealing with treatment and cure of diseases, therapy therefor; pertaining to treatment of disease; e.g., "therapeutic substances" as medicines with an identifiable value in the treatment of diseases of animals; e.g., "therapeutic plasma concentration" as the blood concentration of a drug or substance at which the desired "therapeutic effect" is obtained; e.g., "therapeutics", as a scientific amount for the treatment of disease.

Average dose: the quantify of an agent which will usually produce the "therapeutic effect" for which it is administered.

"Therapeutic dose": a quantity normally several times larger than the "maintenance dose" (i.e., a dose, often a daily dose or dosage regimen, sufficient to maintain at the desired level the influence of a drug achieved by earlier administration of large amounts); except note that in a number of uses, the initial therapeutic dosage utilizing the present invention, continues in subsequent time periods as the maintenance dose as well.

The present invention is a therapeutically and curatively effective fluid treatment composition and medicine which has been used in a productive or therapeutic manner in the following applications:

1. As an enhancing agent working in a synergistic association together with a diverse number of common and commercialized topical skin treatment lotions, cream, ointments, fluids and related compositions; antimicrobial, bacteriocidal, bacteriostatic, and first aid and skin wound healing agents and constituent derivatives of these agents.

2. In promoting soft skin.

3. In killing mold spores and warts on skin and mucosal surfaces.

4. In removing wrinkles and other signs of aging on skin surfaces.

5. In facilitating healthy cell and tissue growth at epidermal and subdermal levels to promote healing of scar tissue and darkened areas resulting from skin burns.

6. For facilitating healing of scrape wounds on skin.

7. In acting as an effective deterrent, repellant and insecticide with respect to various species of insects, and arthropods on skin, hair and fur areas.

8. For facilitating the productive growth of hair on the body, and restoring healthy hair follicles.

9. In the healthy regeneration and growth of fingernails.

10. In facilitating an effective UV ray defense blocker-layer on skin surfaces, and promoting incremental, non-injurious suntanning of targeted skin areas.

11. In aiding productive healing of injured skin on canine, feline and equine skin surfaces and promoting the growth and regeneration of hair and fur; and for effective general veterinary topical skin application, while concurrently constituting a substantially nontoxic agent for mammals.

12. In relieving pain in joints and associated with swelling, improper cellular growth, inflammation, injury or infection; and as an especially effective treatment for such problems in temporomandibular joints and affected adjacent areas.

13. In effectively treating acne in younger and older subjects.
14. In relaxing muscles and associated tension in the neck, shoulder and heavy muscle group areas of the body of animals and humans.
15. In exhibiting the characteristic when used topically on skin of not staining clothing.
16. In promoting the healing and smoothing out of stretch mark areas on body skin surfaces.
17. In exhibiting great heat stability, in absorbing heat generated by elevated temperatures while itself remaining relatively cool in its fluid temperature, while remaining on the skin, and in stabilizing container temperature during elevated temperatures, for example in its use in car, vehicle radiators or in metal, glass or polymer container or fluid housing means.
18. In helping while on the skin, when used in combination with the oral consumption of water, to promote the reduction of sweating.
19. In facilitating the change of hair color from white-gray to a darker color.
20. In promoting healing of insect bite and sting generated damage to the skin of animals or humans.
21. In promoting more quickly obtained, evenly distributed sun tan on the skin with little or no peeling or hypersensitivity on skin surfaces.
22. In promoting shrinking, removal and healing of areas of the skin affected by blisters.
23. In facilitating the softness, healthy appearance, and manageability of human and animal hair/fur, as well as the growth of hair/fur.
24. In promoting closer, less irritating shaving and cutting of human and animal hair.
25. As a means of keeping hands soft when they are utilized in dish soap or other drying environments.
26. In cleaning animate and inanimate surfaces, including fomites, and acting in a microbialcidal and microbialstatic agent.
27. In facilitating the healing of tick-bite wounds in canine species and promoting the dislodging and ejection of tick-head components embedded in canine skin while concurrently helping in healing this same area.
28. In helping to heal herpes virus and other cold sores, boils, blisters and infection associated therein, extending in its effect down to subdermal and dermal areas of the skin including nerve endings.
29. When applied in therapeutic doses in nasal mucosal areas, helping to relieve and clear congestion, or open up, sinus areas.
30. In serving synergistically in combination with hair conditioner and shampoo, enhancing their effect.
31. In serving to lubricate animate and inanimate surfaces.
32. As an infection, antimicrobial mouth wash, when dissolved, for example, in three-drop increments in propositions of about 5 oz. of water, and swirled within the mouth on oral mucosal surfaces without swallowing. Utilized in this capacity, it also helps to relieve toothache and pain.
33. As a synergistic component in hot oil hair treatment.
34. In promoting blood circulation in appendages when applied topically to skin surfaces in these areas.
35. In helping to relieve hypothermia.
36. In killing or reducing the presence of canine flea infestation and flea dermatitis on skin surfaces.
37. In assisting to prevent initial skin contact reaction activating delayed hypersensitivity response thereto, when utilized as a defensive screen on skin surfaces over a given area of the body chosen for protection, for example in seeking to prevent contact allergic response to poison ivy, etc.
38. Utilization in place of or with water, etc., in a spa apparatus to relax areas of the body.
39. When utilized proportionately in water volumes in bathroom commode apparatus, assisting to prevent accumulation of mold, microbial matter and lime deposits.
40. In relieving pain and infection associated with ear and auditory canals, when utilized as an ear drop.
41. In relieving symptoms associated with constipation, when utilized as an oral laxative in proportions of about one teaspoon with about 3 oz. of water.
42. To synergistically enhance the effect of known available mouthwash solutions, when mixed with these agents prior to spraying or application orally.
43. When utilized in proportions of about two (2) teaspoons of invention composition with about one (1) teaspoon of vinegar and two (2) tablespoons of water, ingested orally, improving symptoms of a cold or illness and relieving problems in sinuses.
44. When applied topically, in relieving pain and discomfort of ingrown toenails prior to removal.
45. In relieving pain in subcutaneous and intermuscular injection sites, in cystocyntesis or like procedures involving injection or insertion through the skin into areas of the body with respect to human or animal body surfaces.
46. When applied in cervical, thoracic, lumbar (human) or cervical, thoracic, lumbar, sacral and caudal (animal) spinal areas, helping to induce muscle relaxation, reduction of pain associated with these areas, and promoting a feeling or sensation of relaxation.
47. When utilized topically on the skin, facilitating reduction and healing of age spots, discoloring or dark blemishes and benign growths, on the skin.
48. When utilized sublingually, subpharyngeally or orally, helping to improve symptoms associated with bronchial disorders, coughing, hoarseness and throat and sinus disorders.

It is important to emphasize in utilizing the present invention in each of the uses and applications described that the final binary or tertiary, second stage fluid composition of the present invention, also referenced herein as the #3 or 3-process, is best utilized by mixing the respective phase layers together evenly and uniformly, prior to application, to activate and engage the synergistic effect of multiple layers with each other prior to and at the time of administration.

Some of the synergistic effects obtained in the present processed product, upon remixing as indicated prior to therapeutic application of the invention, include among others the further production of polyiodides more suitable for dissolving and delivery in certain targeted areas; and further production of free or diatomic iodine ($I_2$), increasing the bactericidal effects of the entire remixed fluid product upon therapeutic application.

In a preferred embodiment of the process and connected processed product of the present invention, herein referenced as the "3+" process and product, or processed product, two additional complex-components are added to the earlier described processed product "3", earlier set forth in the specification, to achieve the 3+ processed product.

In the 3+ process and product, the additional components can be added either before or after exposure of the 3-process mixture to a photon component from sunlight. However, it is preferred, and better, consistent results are achieved in adding the additional components after the process mixture of 3 has been exposed to sunlight.

The additional components added to the 1-processed product to obtain the 3+ processed product, are a Beta Carotene/Vitamin A component and a Vitamin $B_1$/Thiamine HCl component.

After the 1-processed product has been exposed to sunlight as indicated, and the reaction products permitted to return to room temperature, and to form either binary or tertiary fluid levels in accordance with the embodiment utilized; about from one (1) 10,000 I.U. to about one (1) 50,000 I.U. increment, or about 6 mg. to about 30 mg., of Beta Carotene component is added to the 1-processed product; and from about one (1) increment of 100 mg. to one (1) increment of about 500 mg. of Vitamin $B_1$/Thiamine HCl, of the powdered form of this component (for best or faster results), is added to the 1-processed product, after which all of the 3+ components are mixed or shaken well.

The Beta Carotene/Vitamin A component can be supplied from a Beta Carotene substance or fluid; or supplied from soybean oil, gelatin form, glycerin form or complex, vegetable oil (such as partially hydrogenated cottonseed and soybean oil), or in a yellow wax form.

It will be observed in adding the additional 3+ components and mixing/shaking that the entire fluid mixed will change from an almond or clear/white color formerly exhibited in the 1-processed product to a yellow-colored 3+ processed product.

As indicated in part earlier, the additional 3+ components may also be added to the 1-process components prior to exposure to sunlight, in which case the 3+ components are exposed to about 45 minutes of natural sunlight, and then about 38 minutes of artificial light, in a room-temperature ambient environment, to achieve the 3+ processed product.

It is important during the 3+ process to monitor the product to confirm that the pH of the 3+ product is found to be at about 5.0. During this monitoring it will be observed or noted that the pH will generally change from a pH of about 6.5 to about 6.8 for the 1-processed product to pH of about 5.0 for the 3+ processed product.

It is important that the final established pH of the 3+ processed product be at about 5.0, as this 3+ embodiment of the present invention is designed specifically for administration into the eyes in drop increments, for treating eye problems and ailments, and especially for treatment of TMJ (temporomandibular joint) pain and problems; and with respect to treatment of problems or pathology on mucosal surfaces. Hence, pH is critically important in these uses of the present invention. In applying the 3+ product for these uses, the 1-processed product components act as a delivery or transport complex for the added 3+ components in effectively delivering them to these preferred areas of targeting, as well as providing additional properties for healing by virtue of the 1-processed product itself.

EXEMPLAR I

Experiment And Use In Effectively Treating Inclusion Cyst And T.M.J. Problems:

A human patient tested, herein referenced as "the patient", had been suffering from a temporomandibular joint disorder and other problems in and around that area with considerable pain and discomfort for a period of time spanning some four (4) years, with traditional medical treatment during about the first year after diagnosis of this patient's problems proving to be unsuccessful.

This patient received a drop of a preferred embodiment, (the 3+ processed product) of the present inventive substance identified in the specification as the "3+" process composition or "processed product", from a small eye dropper, receiving this dose at about six o'clock p.m. on the first day of administration, herein referenced as the first day. A drop of the present composition was placed in each eye of the test subject.

On the next day after administration of the present invention, at about four o'clock p.m. that day, referenced as the second day, the patient experienced a popping sensation from within his left ear, and recovered from this ear shortly thereafter amounts of tissue and blood having the appearance of inclusion cyst, connective tissue and blood substances.

The patient noted on the next day, referenced as the third day, at about ten o'clock a.m., then less than two full days after the first day's administration, the following:

"I felt the drops go down the back part of throat. Teeth hurt and my T.M.J. (temporomandibular joint) the numbness left my upper teeth (gums) (upper) and lower jaw. Ears: I could hear normal again."

During the following several weeks after the first day, the patient's condition continued to improve. During that time, the patient was examined by a Dental Physician, who had previously, some four years earlier, first examined and diagnosed this patient. In a report issued after examination of the patient, the dental physician indicated as follows:

"[The patient] was first seen in our office [over four years ago] as a result of injuries sustained in a vehicular accident [about ten days prior to this first visit]. [The patient's] complaints [at that time] were that of numbness of the upper and lower posterior teeth, pain and pressure in his ears, and pain in the right and left temporomandibular joints. Moderate to severe pain was elicited upon palpation of the following muscles; pterygoids, masseters, temporalis, sternoclei-domastoid, trapezius and the stylomandibular ligament. [The patient] was placed on a soft diet along with a muscle relaxer and was dismissed to return to our office in one week. [At that time, the patient] returned to our office for maxillary and mandibular impressions for the construction of a orthopedic appliance to be worn twenty-four hours a day in order to get the pressure off of his TM joints. This orthotic was seated [about a month later]. We continued to see [the patient from about one week after the seating the orthotic thru a period of about nine months] for physical modality treatments of ultrasound, iontophoresis, high voltage stimulation and thermal therapy. [The patient] tolerated these procedures very well. [The patient] has not been seen in our office since [about four years ago] and has now returned saying he is completely pain free and has been so only since trying a solution [the invention]. This letter [sent] is only to document that I did treat [the patient] for a temporomandibular joint disorder and that he has now returned to my office pain free only after using these eye drops [the invention] and no other temporomandibular joint treatments. [The patient] appears to have normal function and to be pain free."

EXEMPLAR II

Growth Of Human Hair

In tests run with a female human test subject, the subject was given a daily dose of the skin and hair treatment composition of the present invention in the amount of about 2½ grams, a.m., by mouth (oral ingestion). Over the course of about 34 days (first test period), it was noted and recorded that the subject's hair was much more shiny and soft; that hair breakage was less; and that hair growth was faster, with the hair retaining its natural oils better.

Additionally, the same female subject utilized the composition topically on the scalp in daily amounts of about 2½ grams, during a second test period of about 1 month. During this time, the subject used only her previously used, daily hair shampoo. It was observed during this period that her hair was growing twice as fast than previously was the case. It was also noted that the hair was soft and shiny, and easier to style.

Additionally, the same female subject used the composition topically on finger and toenails in daily regiments of about 3 grams; and over a third separate period of time of about a month's time, it was observed that the subject's fingernails and toenails were growing faster than previously noted or observed during a previous 6 month increment of time.

A male human subject, who at one point had lost most of his hair, previously to this observed test period, began using the skin and hair composition of the present invention over a test period of time of about 1 year and 4 months. The composition was applied topically to the scalp in daily amounts of about 3 to 7 grams. After about 7 months of the time period had passed, it was observed that noticeable hair growth had taken place. Throughout the remaining period of the test time it was observed that the subject's hair continued to grow in areas of the scalp which had previously, substantially lost hair growth.

A second female human test subject used the present composition over a period of about 6 months applying the composition to the scalp topically in daily amounts of about 5 to 7 grams, without utilizing any other substances on the hair except fresh tap water. It was observed during the course of this test period that the subject's hair substantially increased in growth and length of hair. It was also observed by male and female test subjects, utilizing the composition as a suntan lotion over 2 to 4 weeks, that hair located in the back of the arms grew longer and became darker in coloration; and the hair growing on stomach and chest areas also grew longer, and became darker in coloration.

Further tests involved a male adult human subject. This subject had, at the time of the tests, lost all hair growth in the lower areas of the forehead scalp portion, and had not experienced any growth in this forehead scalp area for some 4½ years. The subject entered into a first test period of time lasting about 6 weeks. During this test period the subject employed about 6 to 10 grams of the present hair and skin composition, as a daily regimen, applied on a daily basis by spray nozzle container, the daily dose as indicated being applied in the evening each night before retiring. The composition was rubbed into the referenced area of the scalp only moderately, and a wool ski-type hat was placed over the entire scalp area. In employing this daily regimen, it was observed on the 17th day after the first administration commencing the first test period, that about 20 to 30 new hair follicles were beginning to grow in an area where no growth had taken place for some 4½ years. The growth of these hair follicles continued for the balance of the test period, lasting a total of 6 weeks, and at least 10 additional hair follicles beyond the first 20 to 30 initial follicles, were observed to be beginning growth in the observed referenced area of the forehead scalp at the end of the first 6-week period. The subject washed his hair each morning of the first test period with only fresh tap water, utilizing no soaps or shampoos, or other substances, on the scalp area, except the present hair and skin composition applied in the evening of each day as indicated during this first test period.

After this first test period, the subject ceased to apply the composition to his scalp for a period of about 2 months, using only fresh tap water to wash his hair on a daily basis. During this 2 months of time, here referred to as the second time period, there was no further growth of new hair follicles previously observed during the first time period. Additionally, over half of the new hair follicles fell out or were easily removed upon moderate brushing of the forehead scalp area.

One day after the second time period, the subject entered into a third time period of about 3 months where he commenced again on a daily, evening regimen of administering the composition by spray stream to the same forehead scalp area, and covering the scalp each evening before retiring with the previously referenced wool hat.

During this third time period, within the first 3 weeks thereof, continued hair follicle growth in the referenced scalp area was observed, with some 20 to 30 new hair follicles appearing both in the area where growth had remained from the first time period, and in the area where hair follicles had been lost during the second time period. It was clearly observed that there was a net gain of hair growth in this area from the first time period to the third time period. Additionally during the third time period, the new hair follicles, and the old hair follicles from the first time period, were not for the most part removed by moderate brushing. As was the case during the first and second time periods, only fresh tap water was used in the morning of each day of the respective time period for washing the scalp area.

EXEMPLAR III

Growth Of Canine Coat Hair, Healing Of Scratch Wound, And Flea Dermatitis.

The presence of fleas in both dogs and cats as well as other species of animals can be problematic in all areas of the United States, especially in the Southern areas of the country. Fleas are small, wingless, blood-sucking insects with the ability to move very quickly through hair on the coats of animals, and to otherwise utilize the coat hair to escape the effects of substances that might otherwise limit their number or kill the insect. A number of the fleas, sometimes called an infestation of fleas, on the surface skin and hair of the animal, being ectoparasitic, can act as disease carriers to the animals. Species of the flea utilizing the dog and cat as hosts are 'Stenocephalides Felis' (cat, dog) and 'Canis' (dog), among possibly others. Additionally, a number of host-related species of fleas can cause problems in humans and other animal species.

Often, a condition being caused by the presence of fleas on dogs and cats, is flea allergy dermatitis. This condition is characterized by the presence of inflammatory lesions and self-trauma, such as excessive wound-causing scratching and biting, caused by a hypersensitivity to flea bites. In dogs, flea allergy dermatitis frequently appears on the back over the lumbosacral spine, around the base of the dog's tail, or along the length of the tail itself, and inside the hind legs. Secondary infection is commonly associated with flea allergy dermatitis, as is the loss of hair from scratching, biting, wound or infection.

An adult shepherd-type, mixed breed dog of about 6½ years old was made the subject of testing the hair and skin composition of the present invention to determine its effect on flea infestation, flea allergy dermatitis, healing of wounds self-inflicted by the animal because of the allergy, and the growth of hair in the area where hair had been removed by the animal through scratching and biting the area of flea allergy.

The canine subject in this testing had acquired flea infestation, especially in the areas including the middle portion of the tail and the inside of the legs. The subject had acquired as a result of the flea presence, biting and allergy; a fairly acute allergy dermatitis, with considerable discoloration and reddening of the tail and inside rear leg areas. Additionally, the subject had inflicted a fairly severe wound to the middle portion of his own tail with bleeding and later secondary infection. These diagnostic conditions were confirmed by a veterinary physician, but the normal means of treatment which would have included an injection of steroid solution such as cortisone, or other anti-inflammatory agent to prevent further itching, and topical and/or internal administration of a broad-based antibiotic to treat the allergy lesion, wound or secondary infection; were not utilized in this case.

However, in this case, the subject was given topical administration of the present hair and skin composition; first being sprayed on the entire length of the tail and base of the tail with greater concentration being given to the middle portion of the tail over the site of the bite-wound, with 2 to 3 ounces being applied over these areas; and then about 1 ounce being sprayed on the inside portion of each rear leg. After spraying each respective portion as indicated, the composition was carefully and extensively rubbed into the hair and skin of the respective area such that each area was well covered and permeated, down to and over the skin of all referenced, targeted portions. This treatment regimen was utilized in the morning and evening for a test period of time of 4 weeks. Observation of the subject dog revealed that after the first topical administration of the composition on the first day of the test period, the subject dog stopped biting or scratching the wounded tail area or the inside portion of the legs. During the next two days following initial administration, the sizable wound in the middle-tail portion began to close over and heal. Macroscopic observation at the time also revealed that no fleas had remained at or reentered the targeted portions. Throughout the test period and administration of the composition twice a day therein, no fleas were macroscopically observed in the referenced portions.

Throughout the test time period, additionally, the canine subject was never observed biting or scratching the tail portions or inside leg portions. During the test period the discoloration and reddening previously noted in the relevant skin portions changed to normal skin color and texture, with previously existing lesions and secondary infections substantially healing. Also, by the end of the test period, the wound in the tail had completely healed, and the hair in the wound area and inside leg portions had grown back almost to its previously existing length prior to flea infestation and injury. After the test period, the continued administration at least once daily was observed to prevent the return of fleas to the previously treated areas.

Additionally, thereafter, a second test period of 4 days was entered into during which the composition was not utilized in the previously targeted areas. At the end of the second test period, it was observed that the subject dog had again begun to scratch or bite the targeted areas; and it was further macroscopically observed that a plurality of fleas had reentered the area.

EXEMPLAR IV

Utilization And Testing Of Composition As Suntanning Lotion

The test subject for testing the effectiveness of the hair and skin composition as a suntanning lotion, was an adult human male in his mid forties in age. The first test period for testing the present composition in this capacity was for a period of 3 months and 2 weeks. The subject placed enough of the composition on his arms and chest, considered target areas for this testing, to establish a noticeable and viewable, thin film of the composition over the target areas. The first day of the test period, after placing the referenced film of the composition over the target areas, the subject exposed himself to the sun for a 1 hour time period. On the second day of the test period, the subject administered the film of composition on the target areas and exposed himself to the sun for 2 hours. Some redness of the target areas was observed on the first day of the test period, after exposure to the sun, but when additional amounts of 1 to 2 ounces of the present composition were placed on these reddened areas, it was observed that the composition appeared to absorb the redness and the heat perceived to be coming from these reddened areas by the subject. By the second day of the test period it was observed that the referenced redness was gone, and that the subject reported no feeling of soreness or heat in these target areas.

The subject proceeded during daily, small increments of time as the sun was available over the next 19 days of the test time period to administer a film of the composition on the target areas of the skin and expose the areas to the sun. On the twenty-first (21st) day of the test period, the subject was up to a sun exposure time of 3 hours. No redness was observed on the subject's target areas, and it was observed that a brown tan had started to establish itself in the target areas.

On the 34th day of the test time period, it was observed that the previous tanning of 2 weeks earlier had not faded, though the subject was not exposed to any further sun exposure during these times at the target areas. During the next week of the time period it was observed that the administered film of composition appeared to build up a layer of tanning after each application and one-hour time of exposure to the sun at the target areas.

Throughout the balance of the test time period the subject was observed to have developed a very dark tan in the target areas. The subject then entered a second test period lasting about 6 months after the first test period. With no further exposure of the target areas to sun, or daily application of the composition, it was observed that the subject's tan did not fade or diminish in its coloration over the second test period which extended through the winter months.

Additional tests on male and female adult and children subjects over varying time periods and sun exposure verified observed data indicating that a controlled, non-peeling tan could be achieved without redness or soreness, over periods of time as limited as 3 to 4 weeks, which would then last as an observable tan for at least several months without further application of the composition or exposure to sun at respective, targeted areas.

EXEMPLAR V

Repair And Regrowth Of Finger Tissues And Fingernail

The test subject was a young male teenager who had seriously injured and lacerated the end of a finger (middle finger on right hand), such that part of the end of the finger was missing, and very little of the original nail on the finger remained after the injury.

Initially, the test subject was treated by his family doctor to close and suture the injured finger. Seven days after the injury to the finger and administration of suturing, the stitches or sutures were removed from the finger by the physician. From that day forward for a period of 1 month, the finger was soaked on a daily basis, each evening, in about 25 grams of the present hair and skin composition for a period of 2 hours. It was observed during this period of time that the finger appeared to heal faster and more completely to a pre-injury, healthy condition, the fingernail on the previously injured finger appearing at the end of the month as if no previous injury had occurred. Additionally, during the month's period of time during which the finger was soaked in the composition, the sense of feeling, previously lost at the end of the finger due to the seriousness of the original injury, returned to normal; the observation being made at that time that the test subject appeared to have the restoration of normal touch and feeling at the end of this previously injured finger.

EXEMPLAR VI

Treatment Of Ache Conditions

Many different products for the treatment of acne are on the market. Many of the commercially available acne treatment products contain benzoyl peroxide, a topical treatment compound which has a strong tendency to dry out a person's skin. Additional, prescription, medications such as tetracycline have been found to have undesirable side effects, which include among others the unpredictable reactions which can occur with the user's exposure to sunlight on the treatment surfaces. It would appear, in reviewing this data, that a more feasible approach to treating acne in children and adults would be to employ a natural, substantially non-toxic remedy that does not leave the skin excessively dry or flaky.

Accordingly, various test subjects utilized the present hair and skin composition to treat respective acne conditions. Two adult test subjects, male and female, were chosen as tests subjects; and two minor children, male and female, were tested with the composition for the effectiveness in treating acne conditions. In each case it was found that the specific acne condition, an area targeted for testing, disappeared or was substantially improved within 48 hours of treatment, when utilizing a one-time application of the composition, in the amount of 1 to 4 grams, topical application to, and rubbing the composition into the skin surfaces of, the respective targeted areas.

EXEMPLAR VII

Treatment And Injury Protection From Bee Sting And Insect Bites

An adult female human test subject was stung by a hornet. The present composition was utilized in treating the site of injection of the sting and considerable swelling and pain coming from the damaged area. It was observed that the pain and redness was gone from the site of the hornet sting within 7 minutes of topical administration of the present hair and skin composition. It was additionally observed that the test subject was able to stand and walk within 12 minutes of topical administration of the composition to the site of the sting injury.

Another test subject, a minor teenage female, was stung or bitten some 5 times by a plurality of yellow jackets. Upon topical administration of the present composition to the target areas of injury, it was observed that the swelling and pain in the areas of injury had dissipated within 20 minutes of the topical administration of the composition.

Yet another test subject, a male adult, had already applied a film of the composition on the area in question prior to receiving a bee sting to this same area. It was observed that there was essentially no reaction to the bee sting; that within 20 minutes there was only a small appearance of swelling; and that within 1½ hours no sign of the sting remained.

In a similar treatment application utilizing the composition, the test subject was a 3 month old poodle puppy. This subject was observed to have received a bee sting to the left front (or dorsal) paw. The subject was treated by utilizing topical administration of the present composition on the injured target area, and the administration of about 1 cc. of the composition orally. At the time of the sting, and injury to the paw, the puppy would not permit handling of the injured paw without screaming in pain and jerking back the injured paw as part of the pain reaction thereto. Within about 35 minutes of topical and oral administration of the present composition, however, as indicated, the puppy test subject tolerated without noise, movement or jerking reaction the squeezing of the previously injured left front paw; the test subject being observed at this point to be in no further pain or discomfort.

EXEMPLAR VIII

Treatment Of Warts And Mole-like Structures

The test subject was a male adult having a plurality of warts. A small drop of the present composition was applied to each of several warts in a target area of skin. A burning sensation was reported by the subject in the area of topical, drop-increment application. Within 5 days it was observed that the wart could with moderate pressure be scraped off the target area, without damage to the skin in the target area. Within some 6 months after topical administration of the composition to the warts in the target area, the warts previously existing in that area had not returned.

Another male adult test subject topically applied the present composition to a mole-like growth on the subject's right leg on a daily basis, saturating the growth with the composition and rubbing the composition into the growth utilizing three fingers. It was observed that within a month's period of time the growth had completely disappeared.

EXEMPLAR IX

Treatment Of Blisters And Cold Sores

The test subject was an adult male having developed a blister in an area deemed for the testing to be the target area. The present composition was applied topically, directly to the target area in a dosage of about 10 to 15 grams. After 3 such daily topical applications, it was observed that the fluid contained in the blister was being absorbed and the area comprising the original blister target area had diminished in size. Over a further period of time of about 1 week, it was observed that the skin covering the target area could simply be peeled away, and that general healing of the target area proceeded very well and appeared to be healing very quickly.

Additionally, 1 adult female and 2 minor children (male and female), were the subjects over a test period lasting about 2 months and 1 week, during which the respective subjects were treated with the present composition to test its effectiveness in treating cold sores. During the test period each of the 3 subjects developed cold sores in areas on or around their mouth or lips. In each case the composition was utilized in a dosage of about 1 gram topically applied directly to the cold sore target area which involved application to both surface skin and mucosal surface areas. In each case it was observed that the cold sore target area in each subject was effected such that the cold sore completely disappeared, causing each respective subject no further pain or discomfort within the 24 hour period after topical treatment with the composition as indicated. No other substances were employed during the test period to treat the target areas.

EXEMPLAR X

Treatment Of Cuts And Burns

A female adult subject who had accidentally fallen over a roll of barbed wire sustained 2 long cuts each of which was about 3 inches long on her leg. These cuts were of a nature normally requiring suturing, and this was recommended. Instead, however, only the present composition was utilized to treat the cuts. For about 15 days after the injury and severe cuts as indicated, daily topical administration of about 5 grams of the composition was utilized, without utilizing any other substances. It was observed during this test period that dead tissue appeared to flake off around each of the cuts, and the cuts proceeded to heal without leaving a scar in the wound area.

Additionally, each of three tests subjects sustained first degree burns over a 4 month period of time. Each of the subjects administered only the present composition to treat the respective burn injuries. Topical administration of the composition to the burns was in a dosage of from 1½ grams to about 7 grams, placed topically, directly on the burn area. In each case, the burn injury was substantially healed in about 2 days, and in each case no scarring was left in the treatment area as a result of the burn injury.

EXEMPLAR XI

Treatment Of Blood Clots/Spider Veins

The test subject was an elderly adult female. The subject had developed what had been diagnosed as a blood clot, close to the skin surface, on the left leg, close to the knee on this leg. For a test period of time lasting for about 1 week, the subject utilized only the present composition, in daily topical administration of 5 grams of the composition over the area of the clot, constituting the target area for this testing. At the end of the test period of time it was observed that the blood clot had disappeared. Additionally, it was observed that a group of spider-type veins previously located in the target area had also disappeared.

EXEMPLAR XII

Treatment Of Tick Infestation In Dogs And Cats

The first test subject was a male cat having tick infestation. The cat was bathed with normal animal soap shampoo, mixed with about 7½ grams of the composition. A plurality of ticks were observed to dislodge from the test subject, leaving the subject's coat soft and shinny, and upon inspection and observation no ticks were found to remain on the animal. No other substances were utilized with the composition to treat the subject's tick infestation, only the regular animal soap shampoo (which, itself, was not a flea or tick treatment shampoo).

Additionally, a small 1 year old female dog having flea and tick infestation was given a bath combining, as indicated above, normal animal shampoo with about 7½ grams of the composition, every two weeks for a total of three consecutive baths. It was observed at the end of this test period that all ticks (and fleas) had been removed from the animal.

EXEMPLAR XIII

An adult female subject of 75 years of age had on a frequent basis experienced over the last several years of her life reoccurring problems with discolored or black and blue, bruised skin on various areas of her body as a result of inadvertently colliding with inanimate objects or accidently striking an area of her hands, wrists, arms or shoulders while working around her home. In the past, the test subject had endured pain and sensitivity at a bruised site, together with the continued unsightly discolored appearance of the bruise-injury itself, for some two (2) to four (4) weeks for a number of the bruises sustained; before any noticeable healing of the injury was observed. During the test period, the subject injured the top portion of her right wrist, sustaining a significant bruise in this area when a heavy storage box fell on her wrist while she was rearranging stored materials in a closet area. The substantially discolored, dark brown area of injury on the subject's wrist covered an approximate area of about 9 cm. long and about 5 cm. wide over the top portion of the right wrist.

As had frequently been the case with such injuries in the past, the subject had not been able for about two (2) days, after the injury to experience any decrease in the discoloration, swelling or sensation of burning or heat-characterized pain which resulted from this present injury.

On the morning of the third day following the injury, about 3 grams of the present composition was topically applied to the discolored area of the injured wrist, and gently rubbed over and worked into this target area. Within 24 hours of this first application of the composition, the following morning of the next day, (the second day) it was observed that healing of the bruised area had noticeably started, with part of the brown, discolored skin in the target area starting to fade and disappear. Additionally, the subject reported that the sensation of burning or heat-characterized pain had been significantly and noticeably reduced and relieved. During this morning of the second day, a further topical application of about 3 grams of the composition was administered, gently working the composition into the target area. The next morning of the following day (the third day of the test period), the target area was again examined and observed.

On the morning of the third day it was observed that additional portions of previously discolored, injured skin had faded and were healing. The subject reported that most of the heat or burning sensation, which had previously come from the target area, was then almost completely relieved.

The test subject continued to receive daily-morning, topical applications of about three (3) grams of the composition for following daily increments, constituting within the test period a consecutive following fourth, fifth, sixth and seventh day. Upon observation of the target area during each of these days, further fading of skin discoloration and healing of the area were observed and noted by the subject.

On the morning of the eighth day, only one week after starting topical treatment utilizing the composition at the target area, it was observed that the bruised area had substantially healed with no evidence of skin discoloration appearing in the target area. Additionally, the test subject reported that she was experiencing no pain or discomfort from the target area.

In each of the exemplars referenced and described herein, no other substances were used with the present composition to treat the stated applications other than as specifically indicated in each of the respective exemplars.

EXEMPLAR XIV

In testing to determine possible reasons in part why the first phase of the present hair and skin composition changed its color and properties when it was exposed to direct sunlight, changing the composition from a reddish brown to clear/white in coloration, and constituting a critical step in the formation of the second phase of the composition; the emphasis was placed on isolating the components involved in the color change and determining the color change mechanism. Two basic components in the present composition were found to be needed as a part of the reaction with sunlight as a photon source: Cod Liver Oil and Tincture of Iodine and Betadine. Mineral oil or water in the composition was found to dilute the Iodine and hasten the reaction. Both Tincture of Iodine and Betadine separately and/or combined were found to react with Cod Liver Oil when exposed to direct sunlight, and to change color within the composition from brown to clear/white. The concentrations of Iodine/Betadine and mineral oil were found to be important in this photochemical reaction.

This testing utilized the following solutions:

| A | ¼ cup baby oil, 6 drops Iodine |
|---|---|
| B | ¼ cup baby oil, 6 drops BETADINE |
| C | ¼ cup baby oil, 6 drops Iodine, 6 drops BETADINE |
| D | ¼ cup water, 6 drops Iodine |
| E | ¼ cup water, 6 drops BETADINE |
| F | ¼ cup water, 6 drops Iodine, 6 drops |
| G | Tincture of Iodine |
| H | BETADINE |
| I | 50% Iodine BETADINE, 50% Cod Liver Oil |

The containers were set out in the sun and were vigorously shaken periodically. After four hours there was no discernable color change in any of the mixtures except container "I" which had a slight orange tinge. Three drops of Cod Liver Oil were added to all of the containers (except "I") and they were again shaken. After one hour of further exposure the solutions in containers "A", "B", "D", "E" and "F" were white/clear The solution in container "C" was light brown to orange in color and the solution in container "I" had a very slight orange tinge. The color of solution "I" changed from dark red to white over a period of four days of exposure to the sun. Thus, the reaction was pinpointed to that of a reaction between Iodine and Cod Liver Oil caused by exposure to sunlight and hastened by Iodine dilution.

Further research was involved with explaining the reaction between Cod Liver Oil and Iodine. Sunlight was found to be an important ingredient. The phenomenon was explained in several general chemistry and organic chemistry textbooks. The reaction between an iodide ion (or any other halide ion) and an organic compound such as Cod Liver Oil is a nucleophilic reaction. These reactions involve the substitution of one functional group (such as an OH group) by another such as an iodide ion. The reactions are ionic/polar reactions involving the attack by a nucleophile (such as an iodide ion) at a carbon atom within an organic molecule. A functional group attached to the carbon atom is replaced by the iodide ion. This is a competing reaction for the same carbon atom. The nucleophile can undergo displacement or elimination. Therefore, the functional group must be weakly held by the carbon atom for the reaction to proceed at a reasonable rate. Cod Liver Oil is a mixture of several organic molecules with saturated and unsaturated bonds. As a result, there are ample functional groups which can be replaced by iodide ions. Tincture of Iodine and BETADINE both contain diatomic iodine and iodide ions. Sunlight is important in the creation of iodide ions from diatomic iodine. This creation of additional iodide ions allows for a much more efficient nucleophilic substitution for alkyl functional groups in the Cod Liver Oil. Iodine has a reddish brown color. As the iodine is broken down by the sunlight to two iodide ions, nucleophilic substitution occurs. Therefore the color of the solution changes from reddish brown to clear. The mechanism suggests that the only difference between the solution before and after exposure to sunlight is the substitution of iodide ions for alkyl functional groups.

EXEMPLAR XV

Shampoo/Shaving Uses

The test subject, an adult male human, utilized for testing this use, placed about 5 grams of the 1-processed product of the present inventive composition in the palm of his hand and placed the composition on his face, establishing a smooth film across the shaving area of both sides of the face. The subject then added his normally used shaving cream to the areas of the subject's face to be shaved. The subject noted, and it was observed, that a closer more smooth shaving of the subject's beard, without nicks or cutting, appeared to take place, in proceeding to shave the areas covered by the inventive composition-film with the shaving cream as an upper layer, as indicated.

Additionally, within this same genre of use, the present composition was tested for its use with commercially available shampoo products. The test subject was a minor male person. Upon application upon the scalp of the head of the subject of about 2 grams of the hair and skin composition, mixed with a normal daily application of commercial hair shampoo, it was observed after working in and washing off these mixed substances that the hair appeared more shiny and cleaner in comparison to earlier daily applications utilizing only the commercial shampoo.

EXEMPLAR XVI

Ability Of Present Composition To Absorb Heat

In testing to determine additional data with regard to the general heat absorption capacity of the composition in reference to water, about 20 fluid ounces, or about 591 ml., of water was placed in an open-ended oven container under room temperature conditions. Just prior to placing the container and water in the oven, the temperature of the water in its container was recorded to be about 75° F. The water and container were then placed in an oven which had been preheated to about 400° F. as recorded by a separate thermometer device placed inside the oven. Within about 108 minutes, the temperature of the water in the oven had risen from 75° F. to about 212° F., as recorded by a separate thermometer monitoring the temperature of the water, and started to boil. At that time, the water and container were taken from the oven.

The composition of the present invention, the 3–processed product, was placed in a substantially identical open-ended oven container to that used to house the water, of the same size, material and character. The same fluid amount of the composition was placed in the second like container, that being about 20 fluid ounces, or about 591 ml., of the present composition. The temperature of the composition fluid was brought to 75° F. under room temperature conditions. The temperature of the oven was checked and recalibrated to have a preheated temperature of about 400° F., as indicated by the same thermometer device inside the same oven, utilized in testing the water. The composition was then placed in the oven. It was then recorded by a separate thermometer monitoring the temperature of the present composition, that the temperature of the composition in the oven was raised from about 75° F. to about 250° F. in a period of time of about five (5) minutes; and that the temperature of the present composition in the oven further rose from about 250° F. to about 300° F. in five (5) more minutes, or a total elapsed time of about ten (10) minutes to rise from a temperature of about 75° F. to a temperature of about 300° F. When the present composition in the oven reached a temperature of about 300° F., it was observed that the composition was not showing any signs of boiling.

This testing, at least in part, helps to demonstrate the physical and chemical properties of the composition of absorbing greater amounts of heat, more quickly, without boiling. The findings of this test, and other similar tests set forth herein, indicate the important use of the present composition in better stabilizing excessive amounts of heat which could be associated with automotive and engine radiators, or other such compartments needing to utilize a heat stabilizing fluid within a mechanical, chemical, electrical or nuclear system.

While the present invention has been described in connection with the particular embodiments and examples of tests, components and usage thereof, it will be understood that many changes and modifications of this method, product composition and inventive entity may be made by those skilled in the art without departing from the true spirit, concepts and scope thereof. For example, as indicated, other diversified types and kinds of equivalent fluids, solutions and substances can be used in meeting the stuctural and functional inventive purpose and relationship of halogen/halide complex utilized, such as tincture red iodine solution and Betadine solution, and fish liver oil fluid component, as well as dilution components in the invention at least as to the partial effect of mineral oil and water, and the quantum light component of sunlight (though sunlight exposure in the preferred embodiment component of the present invention).

Accordingly, the appended claims, both in their capacity under the patent law as specific claims and as initial specification for matter originally stated therein, are intended to cover all such changes and modifications as falling within the true spirit and scope of the present invention. The reader is, therefore, requested to determine the scope of the invention by the appended claims and their legal equivalents, and not by the examples which have been given.

Having described my invention, I claim:

1. A photochemically processed product for hair and skin treatment, comprising:

Iodine means for providing diatomic iodine and iodide ions;

Fluid means for diluting said iodine means, such that iodide ions are more easily made available for nucleophilic substitution of alkyl functional groups;

a cod liver oil component, said component having a plurality of potentially available alkyl functional groups;

a photon light energy source component photochemically reacting with diatomic iodine in said iodine means to break it down to iodide ions, and making said ions available more rapidly for nucleophilic reaction and substitution on the alkyl functional groups of said cod liver oil component to produce an iodinated cod liver oil product;

said Iodine means and said fluid means being admixed with said cod liver oil component, and, then, exposed to a photon light component such that a first fluid level containing a substantially white/clear iodinated cod liver oil product is irreversibly produced having a pH of from about 6.5 to about 6.8, and a second fluid level is produced containing remaining fluid means, diatomic iodine and iodides, each of said levels being remixed prior to therapeutic application for the treatment of hair and skin, such that the remaining iodinated cod liver oil, fluid means and diatomic iodine and remaining iodides of the photochemically processed product are mixed with each other again and interfaced in secondary contact with one another, for stabilization of pH range, further production of polyiodides more suitable for dissolving and delivery in a therapeutically targeted area and further production of free or diatomic iodine or $I_2$, increasing the bactericidal effects of the entire remixed fluid levels just prior to application.

2. The photochemically processed product for hair and skin treatment, of claim 1, wherein:

said Iodine means comprises a tincture of red iodine component, and a povidone-iodine complex component;

said fluid means comprises a mineral oil component, and a filtered water component; and said photon-light energy source component is a natural sunlight source; directed such that the admixed components are exposed to sunlight for a period of time of from about 15 minutes to about 1 hour.

3. The photochemically processed product of claim 2, wherein:

said admixed components are placed in a container means for housing and supporting the components on a substantially horizontal surface, such that the components are substantially exposed to said light component, said container means housing said components are placed on a substantially horizontal surface;

and said natural sunlight source is directed at least in part toward and upon the housed and supported components by reflecting at least part of the light rays of the sunlight off of a plurality of substantially flat mirrors having one reflective surface, each of said mirrors being placed at least about 18 inches from an adjacent portion of the container, and tilted and secured on the horizontal surface such that the reflective surface faces the container and forms an angle with the horizontal surface of from about 72° to about 78°.

4. The photochemically processed product of claim 1, wherein:

said Iodine means comprises a tincture of iodine component and a povidone-iodine complex component;

said fluid means comprises a mineral oil component and a purified water component; and said photon-light energy source component is an artificial light source directed such that the admixed components are exposed to said artificial light source for a period of time of from about 12 minutes to about 38 minutes.

5. The photochemically processed product of claim 4, wherein:

said artificial light source is an electric lighting component having intensity and lumination at least equivalent to that provided by a 500 watt halogen bulb.

6. The photochemically processed product of claim 4, wherein:
said artificial light source is provided by exposure to light emitted from a nuclear reaction.

7. The photochemically processed product of claim 2, wherein, said components of Iodine means and said fluid means are admixed with said cod liver oil component, prior to being exposed to said light component, in proportions of total weight of admixture comprising:
from about 0.8% to about 1.5% by weight of said cod liver oil component,
from about 1.0% to about 3.0% by weight of said povidone-iodine complex component,
from about 0.9% to about 2.8% by weight of said tincture of red iodine component,
from about 21.0% to about 25.0% by weight of said filtered water component, and
from about 67.0% to about 74.0% by weight of said mineral oil component.

8. The photochemically processed product of claim 7, wherein:
prior to being exposed to said light component, the admixed means and components further include admixed therewith from about 5.0% to about 6.0%, by weight of admixture, of a margarine compound component.

9. The photochemically processed product of claim 8, wherein the admixed components comprise:
from about 4.5 to about 5.0 grams of cod liver oil,
from about 9.0 to about 15.0 grams of povidone-iodine complex,
from about 7.0 to about 13.0 grams of tincture of red iodine component solution,
from about 27.0 to about 29.0 grams of margarine,
from about 111.0 to about 126.0 grams of filtered water, and
from about 362.0 to about 366.0 grams of mineral oil.

10. The photochemically processed product of claim 9, wherein:
the following further components are added to the admixed components after being exposed to said light component, and further mixed:
from about 6 mg. to about 30 mg. of Beta Carotene/Vitamin A component, and
from about 100 mg. to about 500 mg. of Thiamine HCl/Vitamin B component,
such that upon further mixing under room temperature conditions the overall pH of the components is changed to a pH of about 5.0.

11. A photochemically processed product for therapeutic application in hair and skin treatment, comprising:
(a) a cod liver oil component;
(b) a povidone-iodine complex component;
(c) an iodine fluid component, said component being a tincture of red iodine solution;
(d) a filtered and purified water component; and
(e) a fluid petroleum derivative component, said component being mineral oil;
whereby, said components are combined: by admixing to a single fluid phase in a substantially transparent container, and exposing the components in the container to a sunlight source component, having a light wavelength spectrum of at least from about 290 nm. to about 320 nm., for a period of time, to produce the photochemically processed product;
said product having at least binary phase fluid levels, with one of said levels substantially comprising photochemically iodinated cod liver oil, said fluid phase levels being mixed prior to therapeutic application and use for treatment of hair loss, and skin injury and pathology;
wherein:
from about 0.8% to about 1.5% of total admixed weight is cod liver oil component,
from about 1.0% to about 3.0% of total admixed weight is povidine-iodine complex solution,
from about 0.9% to about 2.8% of total admixed weight is tincture of red iodine solution,
from about 21.0% to about 25.0% of total admixed weight is filtered and purified water, and
from about 67.0% to about 74.0% of total admixed weight is mineral oil, and
wherein:
said period of time for exposing said components to a sunlight source is from about 12.0 minutes to about 50.0 minutes, such that the admixed components are irreversibly changed from a generally dark color in their normal unreacted admixed state to a substantially white/clear and gray coloration of respective phase fluid levels in their photochemically reacted and processed state;
the fluid levels of said photochemically processed product being remixed to stabilize overall pH value at from about 6.5 to about 6.8, prior to application, such that the pH of the fluid levels will be more compatible with hair and skin tissue in approaching neutral acid/base pH level.

12. The photochemically processed product for hair and skin treatment of claim 11, wherein:
said components (a) through (e) are admixed in increments proportional to:
from about 0.1 to about 0.2 ounces of cod liver oil component,
from about 0.3 to about 0.4 ounces of povidone-iodine complex component,
from about 0.2 to about 0.3 ounces of iodine fluid component, said component being tincture of red iodine solution,
from about 3.0 to about 5.0 ounces of water component, said component being a filtered and purified water, and
from about 10.0 to about 15.0 ounces of fluid petroleum component, said component being mineral oil; and
wherein:
said processed product further comprises a fatty fluid emulsion component (f), said component being a margarine compound, being added and admixed with the other components (a) through (e) prior to being exposed to said sunlight source, in the amount of from about 0.5 to about 2.0 ounces.

13. The photochemically processed product for hair and skin treatment of claim 12, wherein:
after admixing said components (a) through (f) are exposed to said sunlight source component for the period of time, of from about 12 minutes to about 60 minutes, such that the coloration of the admixed, single fluid phase, components nonreversibly change from a dark coloration to a tertiary phase fluid having a first-bottom level in the container being substantially clear in coloration, a second-middle level being substantially white in coloration and a third-upper level being substantially almond-off-white in coloration, said first-bottom level of the tertiary phase fluid substantially comprising a substantially nonreversible, nucleophilically substituted and iodinated cod liver oil complex which is substantially non-toxic in nature;

wherein:

said tertiary phase fluid is removed from exposure to said sun component and placed under cover from the sunlight in room temperature conditions for a period of time of about 15 to 45 minutes, and wherein:

said tertiary phase fluid is remixed to form a single phase fluid having a white/clear coloration, prior to application.

14. The photochemically processed product for hair and skin treatment of claim 11, wherein:

said components (a) through (e) are mixed in increments proportional to:

about 5.0 milliliters of cod liver oil, from about 10.0 to about 15.6 milliliters povidone-iodine complex, from about 7.4 to about 12.0 milliliters of iodine fluid component, said component being a tincture of red iodine solution, about 120 milliliters of water component said component being filtered and purified water, and about 399.0 milliliters of fluid petroleum component, said component being mineral oil; and wherein:

a further margarine component (f) is admixed with components (a) through (e) prior to exposure to sunlight component, said margarine being admixed in the amount of about 30.0 milliliters.

15. The photochemically processed product of claim 12, for hair and skin treatment, wherein, the following admixed components are utilized:

(a) from about 0.5% to about 1.5% by weight cod liver oil, (b) from about 1.0% to about 3.5% povidone-iodine fluid complex, (c) from about 0.5% to about 3.0% tincture of red iodine solution, (d) from about 4.5% to about 6.0% margarine compound, (e) from about 20.0% to about 24.0% filtered and purified water, and (f) from about 65.0% to about 70.0% mineral oil;

said admixed components, then, being exposed to natural sunlight for a period of time of from about 12.0 minutes to about 50.0 minutes, such that a substantially white/clear product is produced having at least tertiary fluid levels;

said fluid levels being remixed prior to therapeutic application.

16. The photochemically processed product for hair and skin treatment of claim 15, wherein:

said cod liver oil is selected from a group including oil obtained from the liver of cod and related fishes, rich in vitamins A and D, derivatives thereof, said povidone-iodine fluid complex is selected from a group including reaction compounds produced by reacting iodine with the polymer povidone, povidone-iodine fluid complexes, solutions and tinctures and derivatives thereof, said margarine compound is selected from a group including margarines, butters and partially and substantially saturated fatty fluids, oils and emulsions, said filtered and purified water is selected from a group including charcoal-filtered waters and waters substantially filtered, purified and cleaned by other processes, and said mineral oil is selected from a group including mineral oil fluids and solutions and equivalent petroleum derivatives.

* * * * *